US012658327B2

(12) United States Patent
Blackley et al.

(10) Patent No.: US 12,658,327 B2
(45) Date of Patent: Jun. 16, 2026

(54) DETERMINING USER-PERSONALIZED TARGET VALUES OF PRODUCTS USING MACHINE LEARNING MODELS

(71) Applicant: PRESCRYPTIVE HEALTH, INC., Redmond, WA (US)

(72) Inventors: Christopher Scott Blackley, Woodinville, WA (US); Ramakrishnan Iyer, Bothell, WA (US); Luyuan Fang, Seattle, WA (US); Yang Yu, Redmond, WA (US)

(73) Assignee: Prescryptive Health, Inc., Redmond, WA (US)

( * ) Notice: Subject to any disclaimer, the term of this patent is extended or adjusted under 35 U.S.C. 154(b) by 0 days.

(21) Appl. No.: 18/414,366

(22) Filed: Jan. 16, 2024

(65) Prior Publication Data

US 2024/0242849 A1    Jul. 18, 2024

Related U.S. Application Data

(60) Provisional application No. 63/439,269, filed on Jan. 16, 2023.

(51) Int. Cl.
G06Q 30/0283 (2023.01)
G16H 70/40 (2018.01)

(52) U.S. Cl.
CPC ......... G16H 70/40 (2018.01); G06Q 30/0283 (2013.01)

(58) Field of Classification Search
CPC .......................... G06Q 30/0283; G16H 70/40
See application file for complete search history.

(56) References Cited

U.S. PATENT DOCUMENTS

| | | | |
|---|---|---|---|
| 7,895,060 B1 * | 2/2011 | Mahoney ............... | G06Q 10/10 600/300 |
| 8,494,877 B1 * | 7/2013 | Paul ....................... | G06Q 10/10 705/2 |
| 10,818,388 B2 * | 10/2020 | Mahoney ............... | G06Q 10/10 |
| 11,996,203 B2 * | 5/2024 | Moskal .................. | G16H 70/40 |
| 2015/0332422 A1 * | 11/2015 | Gilmartin .............. | G06Q 10/10 705/2 |
| 2016/0092642 A1 * | 3/2016 | Maurer .................. | G06Q 40/08 705/3 |
| 2018/0182477 A1 * | 6/2018 | Mahoney ............... | G06Q 40/08 |
| 2020/0043035 A1 * | 2/2020 | Peysekhman .......... | G06Q 40/08 |
| 2021/0313032 A1 * | 10/2021 | Fotsch ................ | G06F 16/2471 |
| 2025/0014703 A1 * | 1/2025 | Bernstein .............. | G06Q 10/10 |
| 2025/0045620 A1 * | 2/2025 | Sarferaz ................. | G06F 9/451 |

* cited by examiner

*Primary Examiner* — Dylan C White
(74) *Attorney, Agent, or Firm* — Davis Wright Tremaine LLP

(57) ABSTRACT

A set of inputs from a plurality of inputs are selected based on a user identifier of a user. The set of inputs are apportioned and recombined to produce one or more grouped inputs. The one or more grouped inputs are input to one or more machine learning models to provide individualized information output by the one or more machine learning models to the user.

20 Claims, 18 Drawing Sheets

302

301

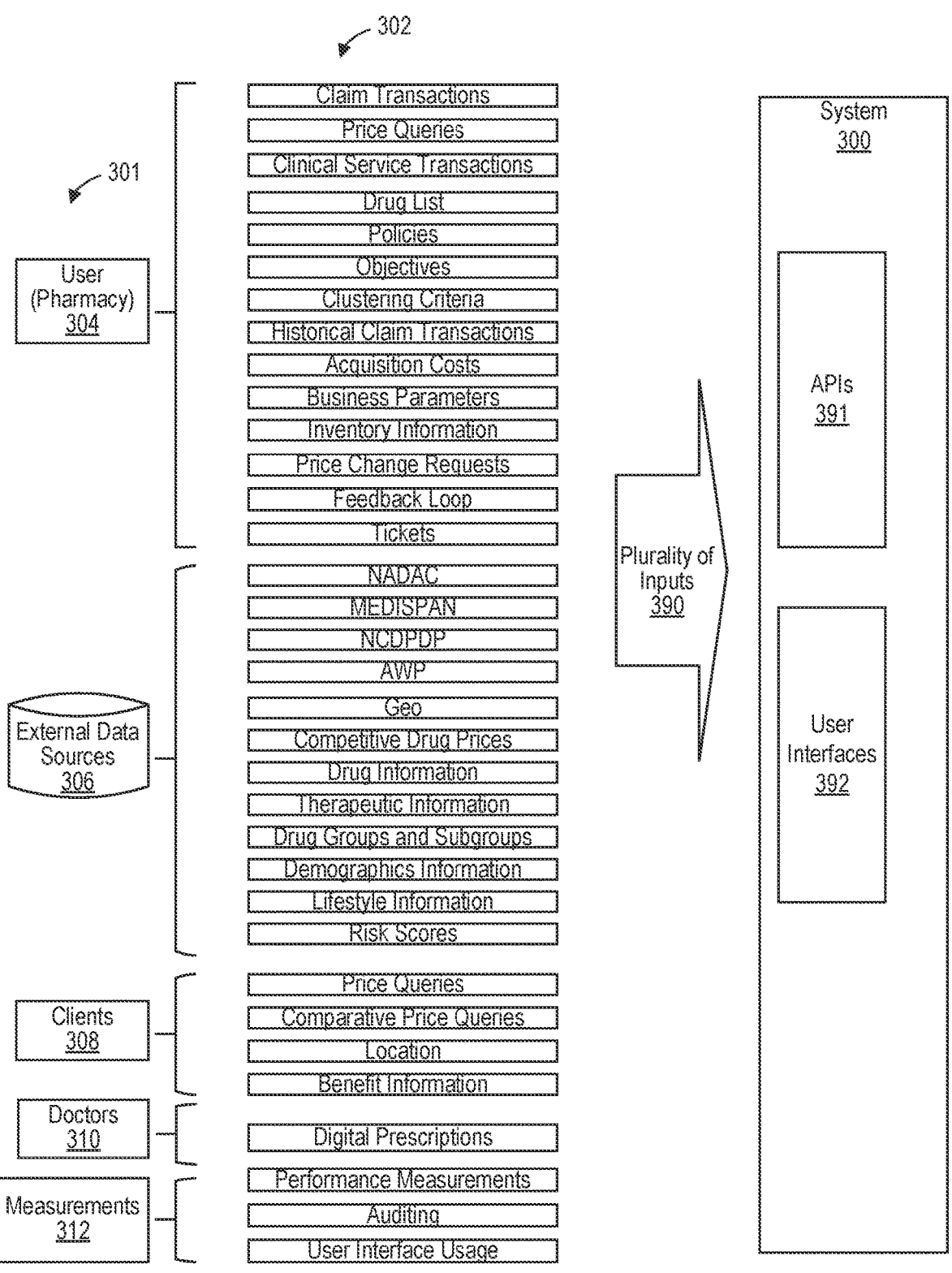

User
(Pharmacy)
304

Claim Transactions
Price Queries
Clinical Service Transactions
Drug List
Policies
Objectives
Clustering Criteria
Historical Claim Transactions
Acquisition Costs
Business Parameters
Inventory Information
Price Change Requests
Feedback Loop
Tickets External Data
Sources
306

NADAC
MEDISPAN
NCDPDP
AWP
Geo
Competitive Drug Prices
Drug Information
Therapeutic Information
Drug Groups and Subgroups
Demographics Information
Lifestyle Information
Risk Scores Clients
308

Price Queries
Comparative Price Queries
Location
Benefit Information

Doctors
310

Digital Prescriptions

Measurements
312

Performance Measurements
Auditing
User Interface Usage

Plurality of
Inputs
390

System
300

APIs
391

User
Interfaces
392

FIG. 3

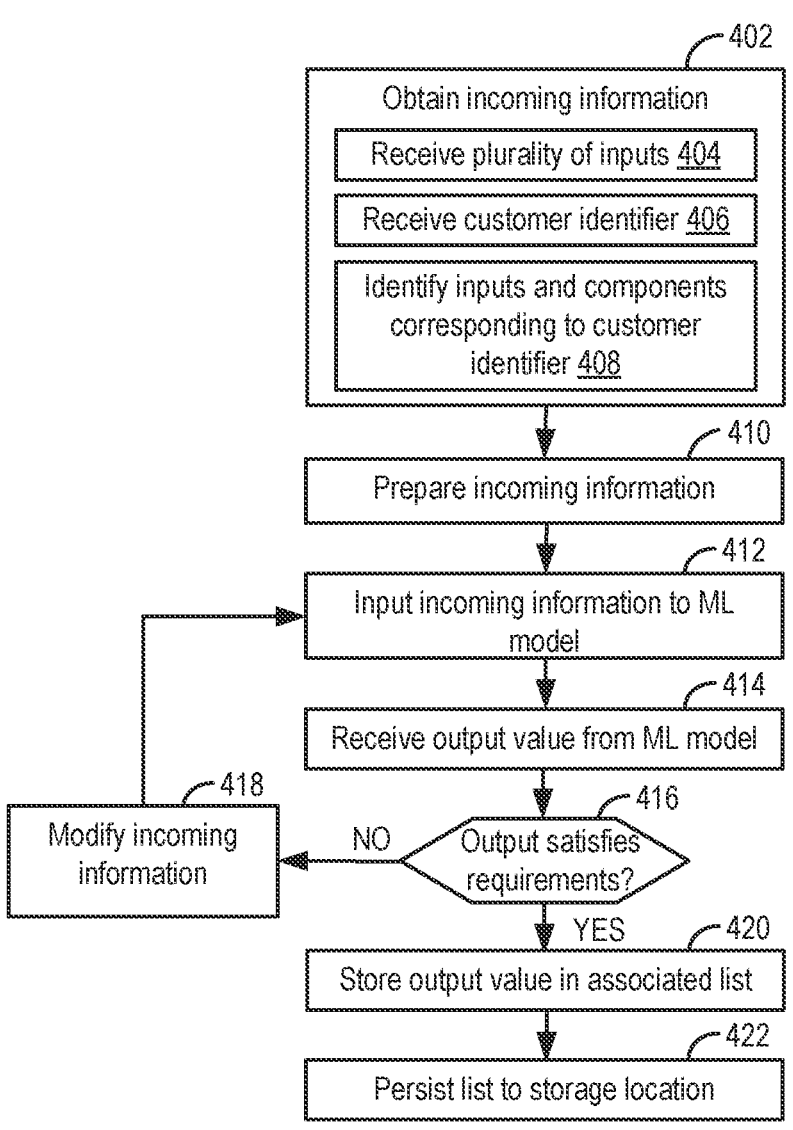
FIG. 4

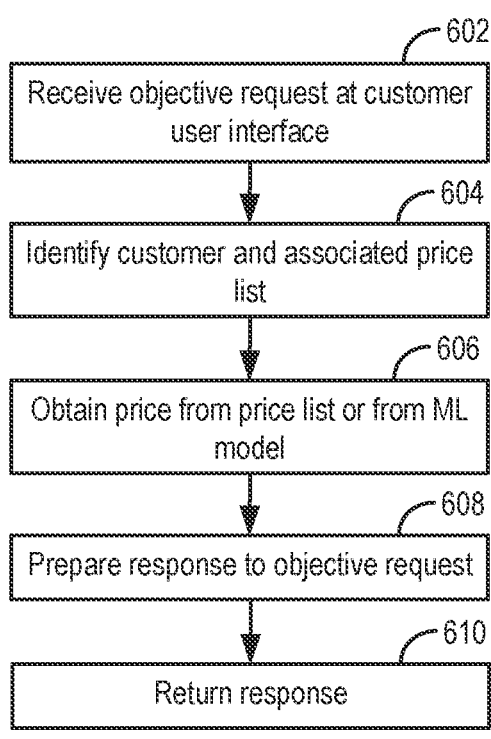
602
Receive objective request at customer user interface
604
Identify customer and associated price list
606
Obtain price from price list or from ML model
608
Prepare response to objective request
610
Return response
FIG. 6

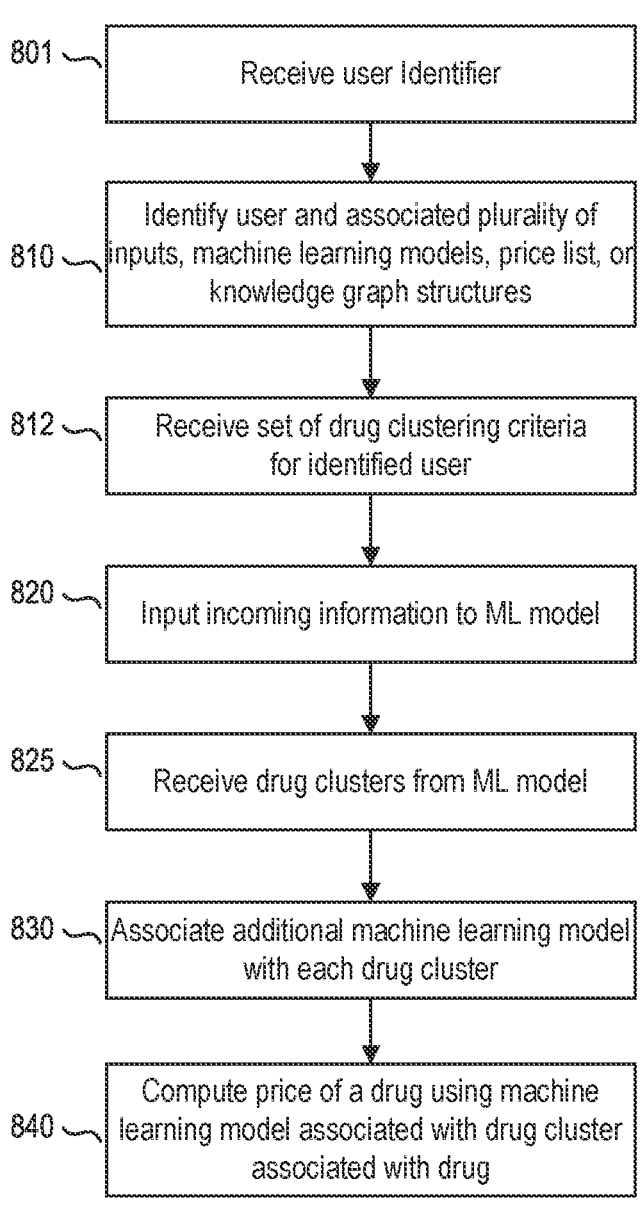

801 — Receive user Identifier

810 — Identify user and associated plurality of inputs, machine learning models, price list, or knowledge graph structures 812 — Receive set of drug clustering criteria for identified user 820 — Input incoming information to ML model 825 — Receive drug clusters from ML model 830 — Associate additional machine learning model with each drug cluster 840 — Compute price of a drug using machine learning model associated with drug cluster associated with drug

FIG. 8

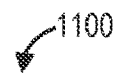

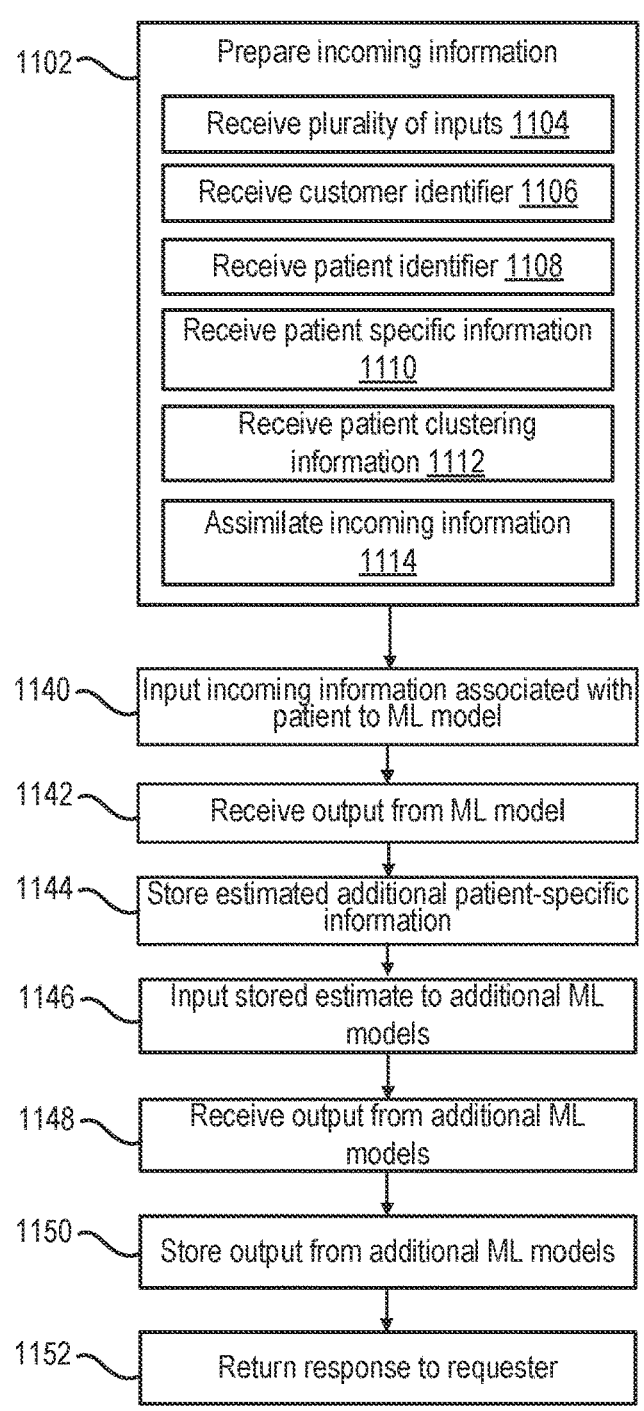

1100

1102 — Prepare incoming information

- Receive plurality of inputs 1104
- Receive customer identifier 1106
- Receive patient identifier 1108
- Receive patient specific information 1110
- Receive patient clustering information 1112
- Assimilate incoming information 1114

1140 — Input incoming information associated with patient to ML model

1142 — Receive output from ML model

1144 — Store estimated additional patient-specific information

1146 — Input stored estimate to additional ML models

1148 — Receive output from additional ML models

1150 — Store output from additional ML models

1152 — Return response to requester

FIG. 11

DETERMINING USER-PERSONALIZED TARGET VALUES OF PRODUCTS USING MACHINE LEARNING MODELS

CROSS REFERENCE TO RELATED APPLICATION

This application claims priority to U.S. Provisional Application No. 63/439,269, filed on Jan. 16, 2023, entitled "SYSTEMS AND METHODS FOR DETERMINING PERSONALIZED OPTIMAL RETAIL VALUE OF DRUGS FOR MULTIPLE TENANTS USING MACHINE LEARNING," the full disclosure of which is incorporated by reference for all purposes herein.

BACKGROUND

Transparency and affordability are longstanding issues in the healthcare industry. For example, the prices of drugs in the U.S. are determined based on various relationships between entities involved, such contracts between pharmacies and Pharmacy Benefit Managers (PBMs) and between PBMs and insurance providers. Efficiently obtaining information regarding available prices for a drug or type of drug that accounts for these relationships is challenging. It may be desirable, therefore, to develop systems and methods to provide individualized information to pharmacies and patients.

BRIEF DESCRIPTION OF THE DRAWINGS

Various embodiments in accordance with the present disclosure will be described with reference to the drawings, in which:

FIG. 3 illustrates an example of a plurality of inputs received by an example system, according to one aspect of the present disclosure;

FIG. 4 illustrates a flow chart of an example method for estimating, recommending, or determining the price of a first product for an identified customer, using a first identified machine learning model processing an identified plurality of inputs, according to one aspect of the present disclosure;

FIG. 6 illustrates a flow chart of an example method for a customer, such as a pharmacy, to send a price query or submit a claim to be adjudicated for a product, according to one aspect of the present disclosure;

FIG. 8 illustrates a flow chart of an example method for clustering products into product clusters, according to one aspect of the present disclosure;

FIG. 11 illustrates a flow chart of example methods for estimating, recommending, or determining the price of a first product personalized to a patient for an identified customer, according to one aspect of the present disclosure;

DETAILED DESCRIPTION

Figure 1:
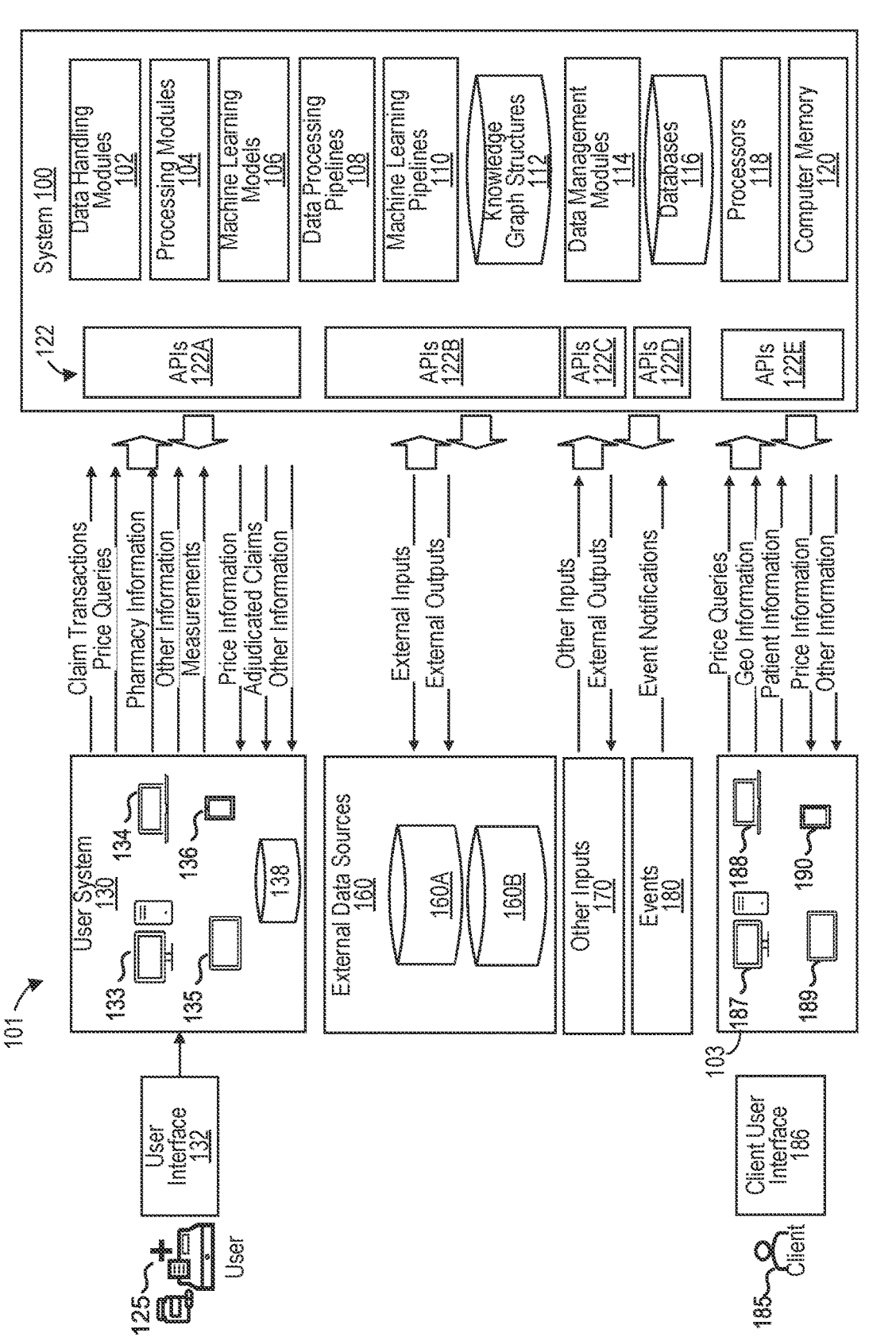
FIG. 1 illustrates an overview and a data flow diagram of an example system for estimating, recommending, or determining the price of a first product for an identified customer, and providing pricing and other information to an identified customer or to a patient, according to one aspect of the present disclosure.

Exemplary embodiments are now described more fully hereinafter with reference to the accompanying drawings, in which some, but not all the embodiments are shown. Embodiments of the present disclosure may be embodied in many different forms and should not be construed as limited to the exemplary embodiments set forth herein; rather, these embodiments are provided so that this disclosure fully conveys the scope of the concepts to those skilled in the art. Disclosed advantages and benefits may apply to only some embodiments of the present disclosure and should not be used to limit the scope of the present disclosure.

Some embodiments may emphasize certain aspects of the present disclosure, and not include others. All embodiments described in this disclosure may be implemented separately, together, or in any combination. Embodiments of the present disclosure may or may not include the features disclosed therein. One embodiment may include additional features, or certain features of another embodiment. Certain features discussed herein with respect to a particular embodiment may be omitted or included in another embodiment. Like reference numbers refer to like, but not necessarily the same of identical elements.

Certain drawings described herein illustrate example data flow diagrams of certain embodiments of the invention. Said data flow diagrams illustrate several data flow steps. Data flow steps may be numbered for illustrative purposes and can occur or be performed in any order. In some embodiments, one or more data flow steps may be omitted, or additional data flow steps may be added, without limitations of the scope of the disclosure. Some drawings described herein illustrated flow charts of example processes of certain embodiments of the present disclosure. Flow charts are described as sequences of block steps. Block steps can occur or be performed in any order; one or more block steps may be omitted, or additional block steps may be added, without limitations of the scope of the disclosure.

The present disclosure describes techniques for estimating prices, recommendations, and other customized information related to products or services offered by vendors to their clients. The present disclosure uses determining prices for prescription drugs as one example application of the techniques described herein. The examples described herein relating to drugs and other healthcare entities, therefore, are provided for illustrative purposes only, and it is contemplated that the techniques described in the present disclosure can be applied to determining target values for various types of products, other items of value, or services provided by healthcare and/or other entities that provide such products, items of value, or services.

Drug price transparency and drug affordability are long-standing issues in the healthcare industry. For example, the prices of drugs in the United State (U.S.) may be determined differently from any other goods. In the U.S. healthcare system, the distribution channels for drugs, and prescription drugs in particular, are generally separate from the payment/reimbursement channels. Drug prices, patient's benefit co-payments, and corresponding pharmacy reimbursements are determined by separate contracts between pharmacies and Pharmacy Benefit Managers (PBMs), and between PBMs and insurance benefit providers.

For example, in the US, drug products are identified by a unique number, called the "National Drug Code (NDC)", which identifies the manufacturer, product code, and package code. The product code identifies the "dosage form", the "strength", and "formulation" of the drug. Examples of "dosage forms" include capsule, tablets, vials, tubes, creams, liquids, solutions, etc. For example, a certain drug may be sold in some dosage forms but not others. In some examples, "strength" refers to the amount of drug in a given dosage form, for example a "500 mg/tablet". For example, a certain drug may be sold in some strengths but not others. The package code identifies the "package size", i.e., how many units of a certain form and strength are in the package, and the "package type", for example a bottle or a carton. For example, a certain drug may be sold in some package sizes and package types but not others. In other examples, the number of units in a package may also be identified as "quantity" or as "days supply", the latter may be defined as the number of days the quantity in the package is supposed to last for a certain number of doses per day. For example, "Prozac, capsules, 20 mg, 30-day supply bottle" may fully identify a particular drug.

Moreover, prescription drugs may have "brand-name" and "generic" versions. For example, a brand-name drug may have one or more generic equivalent. A generic drug may be a medication with the exact same active ingredient, dosage, and strength as its corresponding brand-name drug. A generic drug may be "bioequivalent" to the brand-name drug, meaning that it may have similar chemical properties, such as absorption into the body. A prescription for a certain drug may specify a brand-name drug, or a generic drug, or may leave the option to the pharmacy to choose a brand-name drug of an equivalent generic drug, as the patient prefers. A prescription may omit to specify a manufacturer. In this case, a pharmacy may fill the prescription with a drug made by a manufacturer of their choice. Brand-name and generic drugs may be sold at different prices; for example, generic drugs may be sold at lower prices than their brand-name equivalent; in other examples, drugs made by different manufacturers may be sold at different prices.

For example, a "drug" may not be identified just by its drug name or formulation. Rather, a particular drug may be identified by a combination of some or all the above parameters, such as "brand/generic", "dosage form", "strength", "quantity" or "days supply", and "package type", or other parameters. A "drug" of a certain drug name, formulation, or manufacturer may be sold in different combinations of parameters, and each combination may be sold at a different price. In the present disclosure, a "drug price" may refer without limitation to the price of a specific combination of some parameters for a particular drug. A "drug price" in this disclosure may refer to the price of a specific combination of those parameters for a particular drug including quantity or days supply, or to the "unit price" of a particular drug, i.e., the price of a single unit of the drug. A "drug" in this disclosure may refer without limitation to a prescription drug, a non-prescription drug, an over-the-counter drug, a specialty drug, a controlled substance, an experimental drug, a supplement, an herbal remedy, or any other kind of drug, medication, or remedy.

PBMs are intermediaries which process and adjudicate claims for prescription drug benefits. With respect to prescription benefits, PBMs profit by negotiating contracts that create a margin, referred to as spread, between the price for a drug that an insurance benefit provider pays, including any co-payment, as determined by the contract between a PBM and the benefit provider, and the reimbursement amount due to the pharmacy, as determined by the contract between the PBM and the pharmacy. In case of cash transactions, the margin or spread is created between the retail price of a drug established by the PBM and the reimbursement amount to the pharmacy. Discount cash prices may also be available to patients, said discount prices and corresponding pharmacy reimbursements determined by contracts between PBMs and independent Discount Card Companies, with the PBMs giving part of the spread to the Discount Card Companies for exchange of increased sales volume. Drug acquisition costs for the pharmacies are instead defined by the wholesale distribution network from the drug's manufacturer to the pharmacy.

The contracts between PBMs and pharmacies, between PBMs and benefit providers, and between PBMs and Discount Card Companies are legally protected secrets. The lack of transparency intrinsic in the healthcare drug system, the presence of the PBM intermediaries, and the separation between the distribution and payment channels makes the pharmacy margins razor thin. In some cases, it is even possible that a pharmacy sells a certain drug at a loss, since the contractual reimbursement amount could be lower than the acquisition cost of that drug for the pharmacy, the two amounts being determined by two independent processes. In more general terms, the lack of transparency and complexity of the system may lead to higher drug prices for the patients. The net result may be unaffordable drugs for the patients and pharmacies that struggle to stay in business, all to the advantage of the PBMs and the other intermediaries.

The current healthcare drug system lacks the ability to handle this non-transparency and complexity. Because of secrecy associated with current pricing practices, it is difficult or even impossible to set prices that are at the same time fair, competitive, and optimal, in that they allow pharmacies to stay in business and continue to serve their communities, and at the same time give patients access to drugs at the most affordable price. Note that, as explained above, the healthcare drug system is presented as an example use case for the techniques described in the present disclosure, but it is also contemplated that the same or similar techniques may be applied to determining target values and/or other customized information for other products. For example, the same or similar techniques may be applied for determining pricing and/or other customized information for items such as prescription eyeglasses, hearing aids, prosthetics, mobility devices (e.g., wheelchairs, walkers, crutches, etc.), and so on. Likewise, the same or similar techniques may be applied to determining prices and/or other customized information for "services," such as physical therapy services, professional caregiver services, dental/orthodontic procedures, optometry services, surgical procedures, and so on.

To address these and other challenges, according to one aspect of the present disclosure, a method is provided for obtaining, from a user of a service provider, a request to estimate a set of target values for a set of items that the user provides to clients of the user, the request including a user identifier usable by the service provider to identify the user from a plurality of users of the service provider, identify, from a plurality of machine learning models of the service provider trained to output target value estimations, one or more machine learning models associated with the user, and identify a set of input types used by the one or more machine learning models to estimate the target value. In some examples, a "service provider" refers to a computing resource service provider that hosts and/or offers the system described in the present disclosure to its users. In some examples, a "user" refers to one or more of individuals, computing systems, applications, services, resources or other entities authorized to access the system provided by the service provider. The user may offer products or services to clients of the user. In some examples, a "client" refers to a customer of the user to whom the user offers products or services. The method may further include obtaining a set of input values corresponding the set of input types, apportioning and combining the set of inputs according to predetermined groups to produce one or more grouped inputs, inputting the one or more grouped inputs to the one or more machine learning models, obtaining, as output from the plurality of machine learning models, a set of target values for the set of items, and providing the set of target values to the user.

The system may receive a user identifier that identifies the user, such as a pharmacy, in the plurality of users. In as least one embodiment, the user identifier may be a name, number, code, etc., that distinguishes one user from other users. The user identifier also allows the plurality of inputs to be identified as well as and one or more machine learning (ML) models associated with the user. The user identifier may also be used to identify one or more knowledge graph structures (e.g., semantic networks) associated with the user.

Note that the present disclosure describes utilizing one or more machine learning models at various stages. In some examples, a "machine learning model" refers to a mathematical model of a set of training data. The mathematical model may be built by executing a machine learning algorithm using the set of training data as input. The machine learning model itself may be software performed by processors and/or logic to output a prediction based on a set of inputs that were not necessarily a part of the training data. Such machine learning models may include supervised learning models, unsupervised learning models, semi-supervised learning models, transduction or transductive inference models, reinforcement learning models, and the like. The machine learning models described herein may analyze input data using decision trees, association rule learning, deep learning, inductive logic programming, support vector machines, cluster analysis, Bayesian networks, naïve Bayes classifiers, learning automata, Gaussian process regression, nearest neighbor, random forest, ordinal classification, k-means clustering, lazy learning, artificial neural network, or generally any suitable machine learning algorithm or combination of algorithms. For example, set of decision trees can be generated from historical data by splitting the historical data into subsets based on an attribute value test and partitioned recursively until the splitting no longer adds value to the predictions.

The method may include receiving a plurality of inputs, said plurality of inputs including at least an item list and at least one objective. The plurality of inputs may be related to a set of items provided by a user to clients of the user, where the clients (e.g., patients) may utilize the user (e.g., a pharmacy) and the set of items may include, for example, drug prices, drug recommendations, alternative drugs, other treatments, etc. The plurality of inputs may also include one or more sets of competitive drug prices, said competitive drug prices stating or estimating the sale price of a drug at a pharmacy in a list of competitive pharmacies, or a competition characterization map or score. The plurality of inputs may further include at least one set of claim transaction records, a set of drug acquisition costs, a set of policies, one or more knowledge graph structures, a set of therapeutic data and information, a set of demographic data and information, a set of geographical information, an estimate or a score of the willingness to buy, one or more scores and thresholds representing relevant parameters such as seasonality, and a set of business parameters.

The method may further include running a first ML model associated with the identified user, and processing the associated plurality of inputs. For example, the first ML model may estimate, recommend, and/or determine the price of the first prescription drug in the received input drug list. The method may also include using one or more knowledge graph structure associated with the user in the computation or estimation of the price.

In certain embodiments, the system may further receive at least criteria for clustering an item, such as a set of drug clustering criteria, for the identified user and may run a second ML model associated with the user to group the drugs in the drug list in one or more drug clusters of similar drugs according to the grouping criteria. In these embodiments, a first ML model in a plurality of first ML models may be associated with each drug cluster, instead of a single first ML model used for all drugs. The price of a drug may be computed or estimated by using the first ML model associated to the drug cluster containing that drug.

Other aspects of the present disclosure relate to a system and a method to compute a characterization map or score, such as a competition characterization map or score, which may include a list of competitive users (e.g., pharmacies). The method may include using a third ML model to identify, map and score the user's competition. The method may also include receiving and processing geographical and demographic information to compute the competition characterization map or score. The computed competition characterization map or score may be used by the first ML model to compute the price of a first drug. In certain embodiments, the system may use a fourth ML model to estimate the willingness of users of the identified user to buy a drug.

Other aspects of the present disclosure relate to a system and a method to estimate, determine, and/or recommend a target value or personalized pricing for an identified patient or user. The system may receive a patient identifier identifying the patient and patient-specific information. The patient-specific information may include medical history information, insurance benefit information, demographics information, lifestyle information, therapeutic information, or other information for the identified patient. In some embodiments, said patient-specific information may also be estimated using the method by clustering the patient with patients of similar characteristics using a fifth ML model and assigning the corresponding cluster-specific information to the patient. The method may further include using a sixth ML model to estimate, recommend, and/or determine the price of a first drug using the patient-specific information in addition to the plurality of inputs used by the first ML model. In some embodiment, the method may further include using a seventh ML model to recommend benefit vs. cash payment comparisons, or alternative drugs, or personalized therapeutic information to the identified patient, in addition to the drug price.

According to another aspect of the present disclosure, a system and a method is provided for iteratively determining the optimal price for at least a first drug in a drug list according to at least one optimization criteria for a user in a set of users. The method may work in iterative steps, with each iteration occurring at a configurable, regular frequency, or occurring as triggered by a certain event. For example, at each iteration, the method may include re-computing the prices and identifying a set of recommended price changes that are close to the optimization criteria. The method may further include updating the inputs and re-computing drug clusters until the next iteration is triggered.

At each step, the method may include receiving, in addition to the first plurality of inputs processed by the first ML model, a second plurality of inputs including at least one set of claim transaction records or drug price queries that occurred after the previous iteration of the method and at least one optimization criteria. The second plurality of inputs may also include updated values of the first plurality of inputs associated with the user. The method may include using the first ML model processing the second plurality of inputs to estimate, recommend, or determine a new price for at least a first drug in the drug list associated with the user. The method may include comparing the newly computed prices with the prices computed in the previous iteration and identifying a set of drug candidates for price adjustment as drugs for which the new price brings the computed set of prices closer to at least one optimization criteria. The method may also include updating the prices of the drugs in the set of drug candidates for price adjustment. In some embodiment, the method may further include updating the relevant inputs in the second plurality of inputs and the relevant knowledge graph structures, to be used in the next iteration. The method may further include using the second ML model to recompute the drug clusters, making corresponding adjustments to the drugs in each cluster, and storing the updated drug clusters to be used in the next iteration.

In some embodiments, in the first iteration of the method, a set of historical claim transactions associated to the identified user is included in the plurality of inputs used by the first ML model. In other embodiments, in the first iteration of the method, a set of historical claim transactions associated to the identified user is not included in the plurality of inputs. Other inputs may also not be included in the plurality of inputs, such as policies and prices. In these latter embodiments, a method may include receiving one or more user similarity criteria, identifying clusters of similar users for which those inputs are available, and using an eighth ML model to estimate the relevant plurality of inputs, derived from users in the same cluster of the identified user, to be used by the first ML model to compute drug prices associated to the identified user.

Note that although first, second, third, fourth, fifth, sixth, seventh, and eighth ML models are described above, it is contemplated that a particular implementation may have any combination of one or more of such ML models described above. Further, in some embodiments, a given ML model may be multi-functional in that a single ML model may have combined functionality of one or more of the first, second, third, fourth, fifth, sixth, seventh, or eighth ML models described above.

In further aspects of the present disclosure, systems and methods provide improvements to the estimated, recommended, or determined price of a first drug in response to receiving one or more notifications of certain events, one or more inputs, a feedback signal, a request, or one or more measurements, by re-running the first ML model, or by updating relevant inputs in the first or second plurality of inputs, or by updating relevant knowledge graph structures associated with the identified user.

FIG. 1 illustrates an overview and a data flow diagram of an example system 100 for estimating, recommending, or determining the price of a first drug, and providing pricing and other information to an identified user 125 or to a patient 185, according to one aspect of the present disclosure. The user 125 may be, in at least one embodiment, a customer 125, which may be a pharmacy, or a pharmacy chain, or a group of pharmacies, or an online pharmacy. The customer 125 may utilize system 100 to obtain target values, such as individualized or customized information, to be provided to one or more clients of the customer 125. A patient may be, for example a consumer; a patient may have a medical condition that requires a medication or may be a consumer who may purchase a medication now or in the future, or otherwise has a need to know a price of a drug; a patient in this disclosure may refer without limitation to an entity or an individual associated to an entity who may have a need to know a price of a drug or other information related to a drug.

The system 100 may receive data from various information sources 101, including a customer system, external data sources 160, other inputs 170, events 180, and a patient system 103, and return data to at least some of the information sources 101. In at least one embodiment, the system 100 may be hosted at a computing device, such as a server, or a remote platform, such as a cloud, that is administered and managed by an entity separate from those managing and operating the information sources. The computing device of the system 100 may be communicatively coupled to devices (e.g., computing devices) of the information sources 101 to transmit and receive signals to and from the devices via a remote or hardwired connection. For example, the computing device of the system 100 may be physically coupled to one or more of the devices of the information sources 101 by cables or may be linked thereto by a wireless network or communication link, including but not limited to Bluetooth, radiofrequency, wireless LAN, infrared, microwave, etc. The system 100 may be configured to receive data from the information sources 101, ingest the data, modify the data, and transmit the modified data to at least some of the information sources 101 in response to receiving the data. In at least one embodiment, as shown in FIG. 1, the system 100 may include one or more modules for analyzing, apportioning, assimilating and recombining information received from the information sources 101 to output a value that is optimized for a particular customer or patient.

The system 100 may provide a customer user interface 132 to receive input from the customer 125 and to/display information to the customer. For example, the customer 125, through the customer user interface 132, may enter information for obtaining drug pricing information or may send Rx claim transactions or other information. The customer user interface 132 may be provided to the customer 125 at one or more devices of a customer system 130. The devices may include a computer 133, a laptop 134, a mobile phone 136, a table 135, as well as other devices not shown in FIG. 1. The customer system 130 may further include a database 138 storing information pertaining to the customer 125, including customer preferences and parameters, good and services provided by the customer 125, goods and services used by the customer 125, etc.

The patient system 103 may include various computing devices to support a patient user interface 186 provided by the system 100 that allows the patient 185 to send and receive data to and from the system 100. For example, the patient 185 may enter information for obtaining drug pricing information or other information. The various computing devices may include, for example, a computer 187, a laptop 188, a tablet 189, a mobile phone 190, etc., at which patient information may be stored. The external data sources 160 may include a first external data source 160A and a second external data source 160B, which may be different databases storing different types of data. As an example, the first external data source 160A may store historical data for a class of drugs, and the second external data source may store geographic information regarding popularity of drugs according to geographic region. However, other types of data are possible. The other inputs 170 may include a variety of data relevant to supply, distribution, use, sales, and available of a resource, such as drugs. In at least one embodiment, the other inputs may include values and results output by ML models used to assist in estimating, recommending, and/or determining drug prices and other information. The events 180 may include information regarding occurrences that affect parameters associated with estimating, recommending, and/or determining drug prices and other information.

The system 100 may further provide a plurality of application programming interfaces (APIs) 122 to facilitate exchange of data between the system 100 and the information sources 101. In at least one embodiment, the system 100 may include a first API 122A for interfacing with the customer system 130, a second API 122B for interfacing with the external data sources 160, a third API 122C for interfacing with the other inputs 170, a fourth API 122D for interfacing with the events 180, and a fifth API for interfacing with the patient system 103. The plurality of APIs 122 channel information to be processed by components of the system 100. In at least one embodiment, the components include data handling modules 102, processing modules 104, ML modules 106, data processing pipelines 108, ML pipelines 110, knowledge graph structures 112, data management module 114, databases 116, processors 118, and computer memory. Each component may be configured to perform specific tasks with respect to the methods described further below.

The system 100 may receive inputs from the information sources and return outputs to one or more of the information sources. For instance, the customer system 130 may transmit one or more of claim transactions, price queries, pharmacy information, other information, and measurements to the system, through the first API 122A. The system 100 may return, for example, price information, adjudicated claims, and other information to the customer system 130 to be displayed at the customer user interface 122. The system 100 may also receive external inputs from the external data sources 160 and return external outputs thereto via the second API 122B, receive inputs and return outputs to and from the other inputs 170 via the third API 122C, and receive event notifications from the events 180 via the fourth API 122D. The patient system 103 may similarly send inputs, such as price queries, geographical information, and patient information to the system 100 and receive price information, and other information from the system 100 via the fifth API 122E. It will be appreciated the components of the system 100 shown in FIG. 1 are not representative of an exhaustive list of components that may be included, and more or less components may be present, in other examples.

Figure 2:
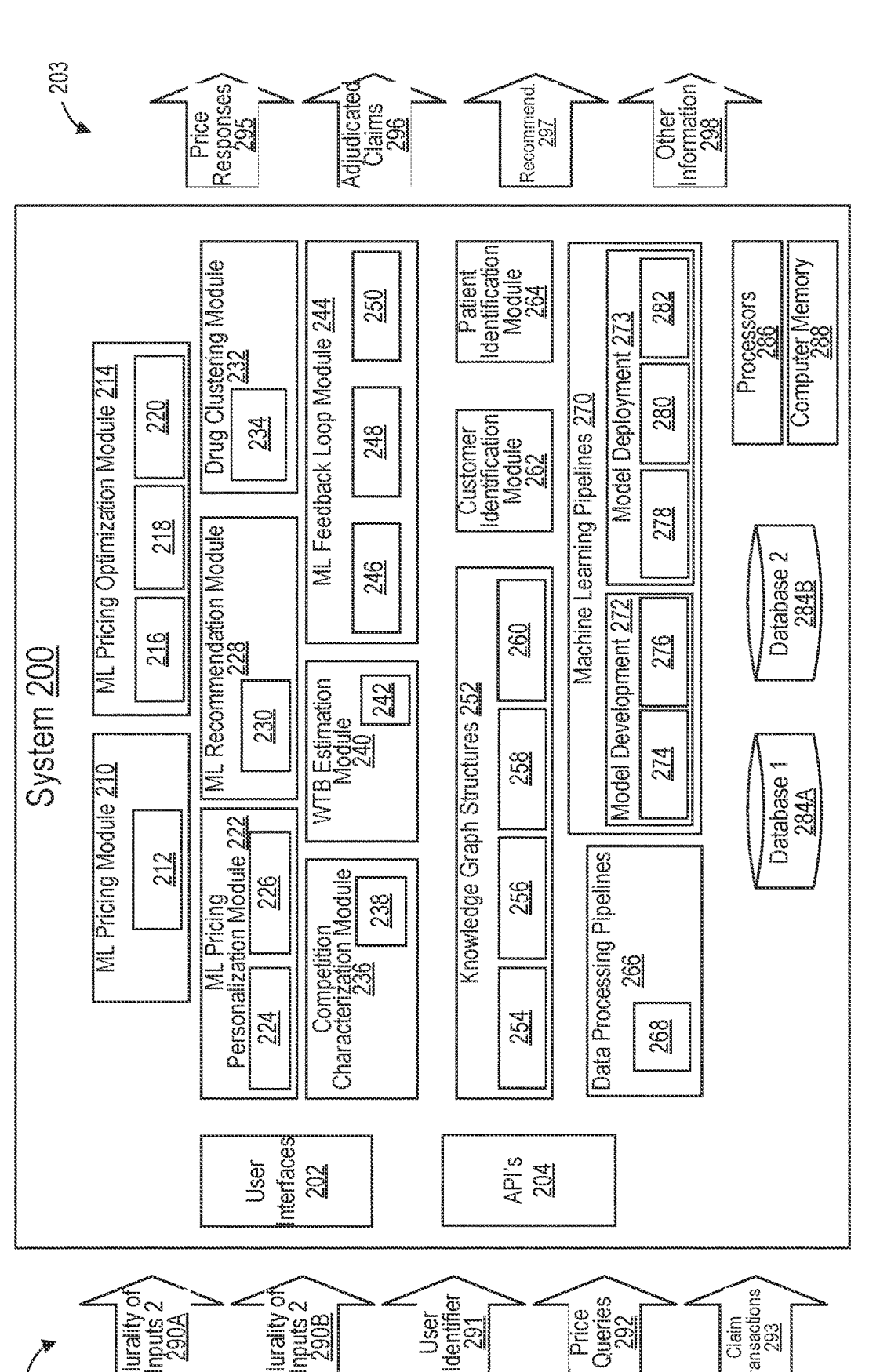
FIG. 2 illustrates a block diagram of an example system for estimating, recommending, or determining the price of a first product for an identified customer, and providing pricing and other information to an identified customer or to a patient, according to one aspect of the present disclosure.

FIG. 2 illustrates a block diagram of an example system 200 for estimating, recommending, and/or determining the price of a first drug for an identified customer, and providing pricing and other information to the identified customer or to a patient, according to one aspect of the present disclosure. In at least one embodiment, the system 200 may be an embodiment of the system 100 of FIG. 1. Incoming information 201 to the system 200 may include a first plurality of inputs 290A, a second plurality of inputs 290B, a customer identifier 291, price queries 292, claim and transactions 293. Outgoing information 203 from the system 200 may include price responses 295, adjudicated claims 296, recommendations 297, and other information 298. The incoming information 203 may be received from one or more of the information sources 101 of FIG. 1 and the outgoing information may be delivered to one or more of the information sources 101 of FIG. 1.

The system 200 may include components such as user interfaces (similar to the customer user interface 132 and the patient user interface 186 of FIG. 1), and APIs 204, which may be similar to the plurality of APIs 122 of FIG. 1. The components may further include various ML modules such as a ML pricing module 210, which may include a first ML model 212, a drug clustering module 232 which may include a second ML model 234, competition characterization module 236 which may include a third ML model 238, and a willingness to buy estimation module 240 which may include a fourth ML model 242. The ML modules may further include a ML pricing personalization module 222 which may include fifth and sixth ML models 224 and 226, a ML recommendation module 228 which may include a seventh ML model 230, a ML pricing optimization module 214 which may include a Warm start module 216, a Subzero start module 218, and an eighth ML model 220, and a ML feedback loop module 244 which may include a feedback processing module 246, a price change request processing module 248, and a measurement module 250.

The components may also include knowledge graph (KG) structures 252, which may include a prescription KG 254, a geographical KG 256, a willing to buy graph 258, and a personalization KG 260. The components may also include a customer identification module 262 and a patient identification module 264. The components of the system 200 may further include data processing pipelines 266 which may include a data cleaning and preparation module 268, and machine learning pipelines 270 which may include model development 272 and model deployment 273.

The incoming information 201 may be processed by the system 200, which may include extracting, separating, grouping, performing computations, and/or compiling the incoming information 201 according to data provided by the incoming information 201. This may include receiving, from the incoming information 201, an indication of a target value or set of data that is to be output as the outgoing information 203 from the system 200.

Multi-dimensional data points may be obtained from the incoming information 201 and weighted connections between the data points may be captured and represented by system 200 in the KG structures 252, and used for ML modeling and engineering. The ML models 212, 234, 238, 242, 224, 226, 230, and 220 may use one or more multi-dimensional data points from the KGs and/or other data sources to generate predicted value drug prices for consumer retail. The ML models may process one or more available incoming signals and locate drug prices that satisfy constraints such as pharmacy's policies, according to one or more objectives (e.g., improve pharmacy's profitability) or metrics provided in the incoming information 201.

FIG. 3 illustrates an example of a plurality of inputs 390 that may be received by an example system 300 according to one aspect of the present disclosure. In at least one embodiment, the plurality of inputs 390 and the system 300 may be examples of information input from information sources 301, some of which may be similar to the information sources 101 of the system 100 of FIG. 1. The system 300 may receive input variables 302 from devices of information sources, similar to the information sources 101 of FIG. 1, including devices of one or more of the information sources 301, including a customer 304, external data sources 306, patients 308, doctors 310, and a source of measurements 312.

The input variables 302 which may be included in the plurality of inputs 390 and received by the system 300 from the customer 302 may include one or more of claim transactions, price queries, clinical service transactions, drug lists, policies, objectives, clustering criteria, historical claim transactions, acquisition costs, business parameters, inventory information, price change requests, feedback loops and tickets. The system may also receive, as the plurality of inputs 390, one or more of data from National Average Drug Acquisition Cost (NADAC), from Medi-span, data from the National Council for Prescription Drug Programs (NCPDP), data from Average Wholesale Price (AWP), geographic information, competitive drug prices, drug information, therapeutic information, drug groups and subgroups, demographic information, lifestyle information, and risk scores from the external data sources. The plurality of inputs 390 may also include input variables 302 from the patients 308 which may include price queries, comparative price queries, location information, and benefit information, as well as input variables 302 from the doctors 310 such as digital prescriptions. Further, the system 300 may receive, as the plurality of inputs 390, input variables 302 from the measurements 312 such as performance measurements, auditing information, and information regarding user interface usage.

The plurality of inputs 390 may be received by the system 300 through APIs 391, which may be similar to the plurality of APIs 122 of FIG. 1 and the APIs 204 of FIG. 2, and user interfaces 392, which may be similar to the customer user interface 132 and the patient user interface 186 of FIG. 1, and the user interfaces 202 of FIG. 2. The system 300, although not illustrated in FIG. 3, may further include additional components, such as those depicted in FIGS. 1 and 2.

FIG. 4 illustrates a high level flow chart of an example method 400 for estimating or determining the price of a first drug for an identified customer, using a first identified machine learning model processing an identified plurality of inputs. Related methods are depicted in FIGS. 5-15, which either illustrate processes that may be included in method 400 or may be performed in conjunction with, in parallel with, or independent of method 400. In at least one embodiment, a processor of a system, such as the processors 118 and 286 of FIGS. 1 and 2 and the systems 100, 200, and 300 of FIGS. 1-3, as well as those of FIGS. 16-18, may perform one or more steps of the methods of FIGS. 4-15 using one or more components described in FIGS. 1-3 and 16-18. In at least one embodiment, one or more steps of method 400, as well as the methods of FIGS. 5-15, are otherwise combined, performed in series, and/or performed in parallel. In at least one embodiment, some or all of method 400 (or any other methods described herein, or variations and/or combinations thereof) is performed under control of one or more computer systems, such as a computing device illustrated in FIG. 18, configured with computer executable instructions and is implemented as code (e.g., computer executable instructions, one or more computer programs, or one or more applications) executing collectively on one or more processors, by hardware, software, or combinations thereof. In at least one embodiment, code is stored on a computer-readable storage medium in form of a computer program comprising a plurality of computer-readable instructions executable by one or more processors. In at least one embodiment, a computer-readable storage medium is a non-transitory computer-readable medium. In at least one embodiment, at least some computer-readable instructions usable to perform the method of FIGS. 4-15 are not stored solely using transitory signals (e.g., a propagating transient electric or electromagnetic transmission). In at least one embodiment, a non-transitory computer-readable medium does not necessarily include non-transitory data storage circuitry (e.g., buffers, caches, and queues) within transceivers of transitory signals. In at least one embodiment, the methods of FIGS. 4-15 performed at least in part on a computer system such as those described elsewhere in this disclosure. In at least one embodiment, logic (e.g., hardware, software, or a combination of hardware and software) performs the methods of FIGS. 4-15.

Turning to FIG. 4, at step 402, method 400 includes obtaining incoming information from various information sources. In at least one embodiment, the information sources may include one or more of the information sources 101 of FIG. 1 and 310 of FIG. 3. Obtaining the incoming information may include receiving a plurality of inputs at step 404, which may include any combination of the plurality of inputs 390 of FIG. 3. The plurality of inputs may include at least a drug list and an objective (e.g., a request for a specific outcome). The plurality of inputs may also include one or more sets of competitive drug prices, said competitive drug prices stating or estimating the sale price of a drug at a first pharmacy in a list of competitive pharmacies, or a competition characterization map or score. The plurality of inputs may further include at least one set of claim transaction records, a set of drug acquisition costs, a set of policies, one or more knowledge graph structures, a set of therapeutic data and information, a set of demographic data and information, a set of geographical information, an estimate or a score of the willingness to buy, one or more scores and thresholds representing relevant parameters such as seasonality, and a set of business parameters. In at least one embodiment, the plurality of inputs may also include data estimated, recommended, and/or determined by one or more ML models of the system that may provide data complementary to the plurality of inputs.

Obtaining the incoming information may also include receiving, at step 406, a customer identifier that identifies the customer, such as a pharmacy, from a plurality of customers provided by the information sources. The customer identifier may be used, at step 408 of method 400, to select inputs from the plurality of inputs and the one or more ML models corresponding to the customer identifier and the objective. The customer identifier may also be used identify one or more knowledge graph structures associated with the customer. In at least one embodiment the incoming information may be received by one or more APIs which may distribute the incoming information to suitable components of the system for further processing.

At step 410, method 400 may include preparing the incoming information that has been received, identified, and/or selected. Preparing the incoming information may include processing and cleaning the information. For example, at least a portion of the incoming information may be distributed to data processing pipelines to be cleaned and prepared by a data cleaning and preparation module (e.g., the data processing pipelines 266 and data cleaning and preparation module 268 of FIG. 2). The information may be cleaned by removing or omitted extraneous or nonrelevant data from the incoming information and may prepare the incoming information by slicing (e.g., apportioning) the information into smaller segments based on content and/or data type. Preparing the incoming information may further include modifying a format of the data, which may be heterogeneous and derived from disparate information sources utilizing different formats, syntax, language, etc., to allow the segments to be recombined. In at least one embodiment, the segments may be recombined according to similarly and/or relevancy to apply predetermined groupings (e.g., categories/classifications) of the data. For example, applying the predetermined groupings may produce one or more grouped inputs of the plurality of inputs. In at least one other embodiment, preparing the incoming information may further include converting the data to a format recognized and using by one or more ML models of the system.

At step 412, method 400 may include providing the prepared incoming information to the one or more ML models. In at least one embodiment, the one or more ML models may include any combination of the ML models depicted in FIG. 2. As one example, the one or more ML models may include the first ML model 212 of the ML pricing module 210 of FIG. 2. The incoming information, including the plurality of inputs, the objective, and the customer identifier, may be used by the one or more ML models to provide one or more of an estimation, a recommendation, and a determination of a value corresponding to the objective. In at least one embodiment, the objective may be to obtain an optimized price for a prescription drug and the one or more ML models may output a price of the prescription drug. The one or more ML models may also use one or more KG graphs corresponding to the customer identifier to generate the estimation, recommendation, and/or determination of the value.

At step 414, method 400 may include receiving a value output by the one or more ML models. In at least one embodiment, the value may be a drug price. In other embodiments, however, the value may be any recommendation, estimation, and/or determination provided by the ML model based on the incoming information input to the ML model. In at least some other embodiments, the value may be a predicted likelihood of a particular side effect of a drug, a predicted list of side effects of a drug or treatment, predicted optimal treatment times for a treatment or drug, predicted interactions between drugs, etc.

At step 416, method 400 may include confirming if the output value satisfies requirements indicated by the incoming information. For example, the requirements may include policies and constraints arising from the plurality of inputs used to generate the output data. As an example, the plurality of inputs and/or objective may indicate that the drug prices are to be below a threshold price, or, as another example, that a list of three drugs fulfilling the policies and constraints are desired. If the output value does not satisfy the requirements, method 400 may include proceeding to step 418 to modify the incoming information to be input to the one or more ML models. In at least one embodiment, modifying the incoming information may include adjusting the plurality of inputs to re-compute the value output by the one or more ML models.

For example, at least a portion of the plurality of inputs may be re-selected to alter the incoming information. This may include selecting input variables of the plurality of inputs that, as an example, may lower an output drug price. As another example, the plurality of inputs may be adjusted to allow a second drug and corresponding drug price to be output by the one or more ML models in addition to a first drug and corresponding drug price that was previously output by the one or more ML models. In at least one embodiment, modifying the incoming data may include inputting relevant data to additional ML models of the one or more ML models that may provide recommendations, and estimations that are complementary to the those of the one or more ML models of the system. For example, the additional ML models may be any combination of the ML models 220, 224, 226, 230, 234, 238 and 242 of FIG. 2. Method 400 may include returning to step 412 to input the modified incoming information to the one or more ML models.

If the output value satisfies the requirements at step 416, method 400 may include continuing to step 420 to store one or more output values in an associated list. In at least one embodiment, the one or more output values may be stored in a list of drug prices for one or more drugs. At step 422, method 400 may include persisting the list to a storage location, such as a memory or a database hosted at a computing device. In at least some embodiments, the list may be displayed to a customer or a patient at a user interface.

In at least some embodiments, the system may be configured to compute or estimate the price for a drug, multiple drugs, or all the drugs in a drug list included in the plurality of inputs. The system may compute the price of all the drugs in the drug list in advance or compute the price of a drug upon receiving a claim or a price query for that drug. The system may compute the prices of all the drugs in the drug list at regular, configurable intervals of time, or compute prices continuously, as it receives new claim transactions.

Figure 5:
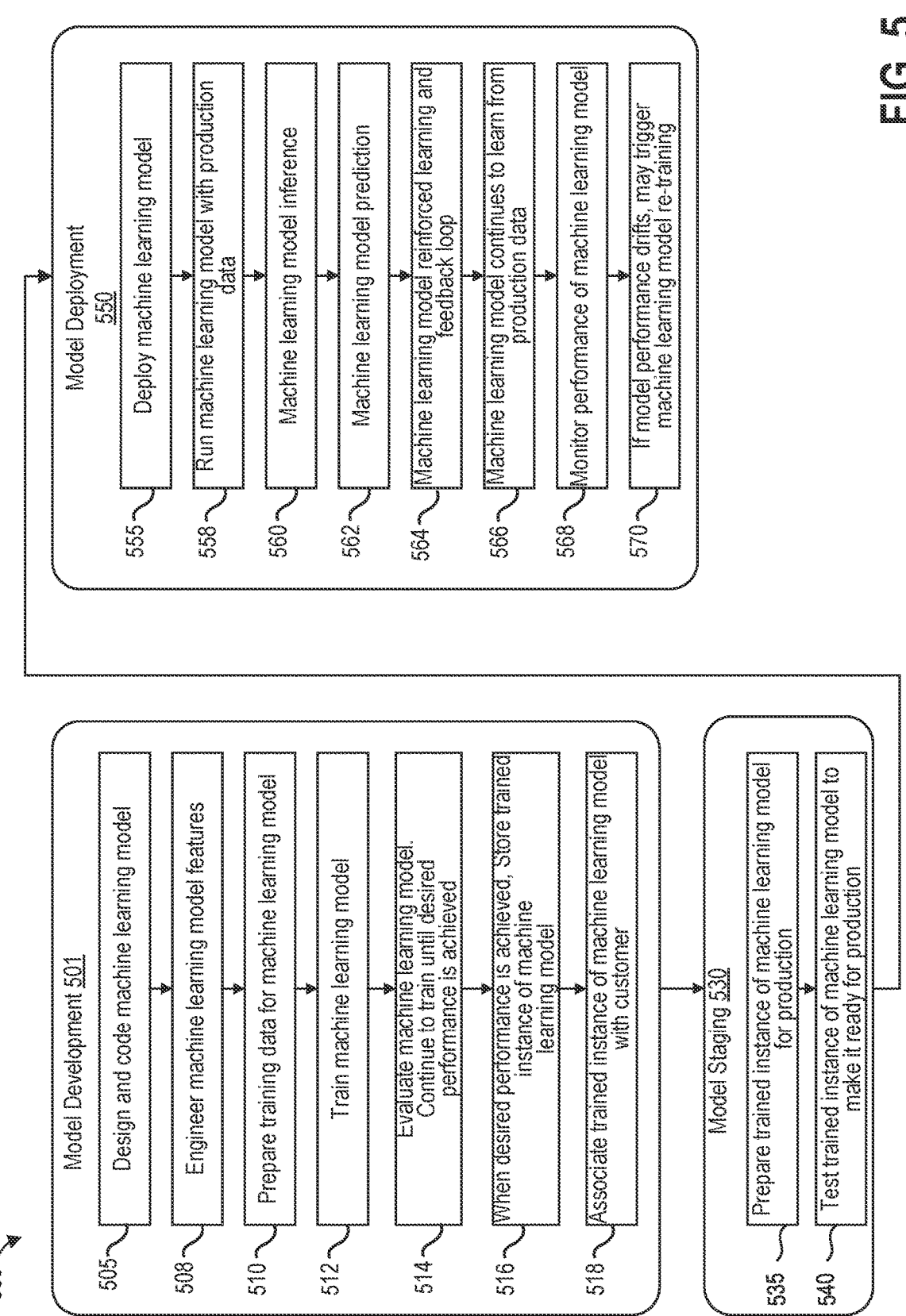
FIG. 5 illustrates a flow chart of for training and deploying a machine learning model, and continuing to update the machine learning model using real data in a system, according to one aspect of the present disclosure.

FIG. 5 illustrates a flow chart of example method 500 of training and deploying a ML model, where the ML may continually be updated using from data obtained by a system, according to one at least one embodiment of the present disclosure. The system may be similar to the systems 100, 200, and/or 300 of FIGS. 1-3. In at least one embodiment the ML model may be any one of the one or more ML models deployed in method 400 of FIG. 4 and depicted in FIG. 2. Method 500 may include three portions including model development 501, model staging 530, and model deployment 550.

During model development 501, method 500 may include designing and coding the ML model at step 505, engineering ML model features at step 508, preparing training data for the ML at step 510, and training the ML model using the training data at step 512. Model development 501 may further include, at step 514, evaluating the ML model and continuing to train the ML model until a desired performance is achieved, such as when convergence is attained. Method 500 may include storing a trained instance of the ML model at step 516 and, at step 518, associating the trained instance with a customer.

Method 500 may include proceeding to model staging 530, where, at step 535, method 500 may include preparing the trained instance of the ML model for production. Model staging 530 may further include testing the trained instance of the ML model, at step 540, to ensure the ML model is fit for production.

Method 500 may include continuing to model deployment 550, which may include deploying the ML model at step 555, running the ML model with production data at step 558, performing inference using the ML model at step 560, and generating a prediction using the ML model at step 562. Model deployment 550 may further include, at step 564, reinforcing learning of the ML model and using a feedback loop, continuing to train the ML model on production data at step 566, monitoring a performance of the ML model at step 568, and trigger re-training of the ML model if the performance is detected to drift (e.g., degrade) at step 570.

FIG. 6 illustrates a flow chart of an example method 600 for submission of a request for an objective to be fulfilled, such as a price query or adjudication of a claim, to a system, such as any of the systems 100, 200, 300, 1600, and 1700 of FIGS. 1-3, and 16-17, to obtain an output value from the system, according to at least one embodiment of the present disclosure. The objective may be submitted by a customer at a customer user interface provided by the system (e.g., the customer user interface 132 of FIG. 1, the user interfaces 202 of FIG. 2, or the user interfaces 392 of FIG. 3) and received by one or more APIs implemented by the system.

At step 601, method 600 may include receiving a request indicating an objective at the customer user interface from the customer. The objective request may be submitted in conjunction with a plurality of inputs and a customer identifier, as described above with reference to method 400 of FIG. 4, and may be used to identify the customer and a price list associated with the customer at step 604. At step 606, method 600 may include obtaining a price from the associated price list, in one example. In another example, the price may be obtained from one or more ML models, as described above with reference to method 400 of FIG. 4. For example, the one or more ML models may compute the price in real-time in response to submission of the requested objective.

At step 608, method 600 may include preparing a response to provide to the customer. In at least one embodiment, the objective may be a price query and the price obtained at step 606 may be prepared to be presented to the customer. In at least one other embodiment, the objective may be adjudication of a claim transaction. To adjudicate the claim transaction, the price obtained at step 606 may be used and the adjusted claim transaction may be stored at a storage location of the system, for example. At step 610, method 600 may include returning the response to the customer by displaying the response to the requested objective at the user interface.

Figure 7:
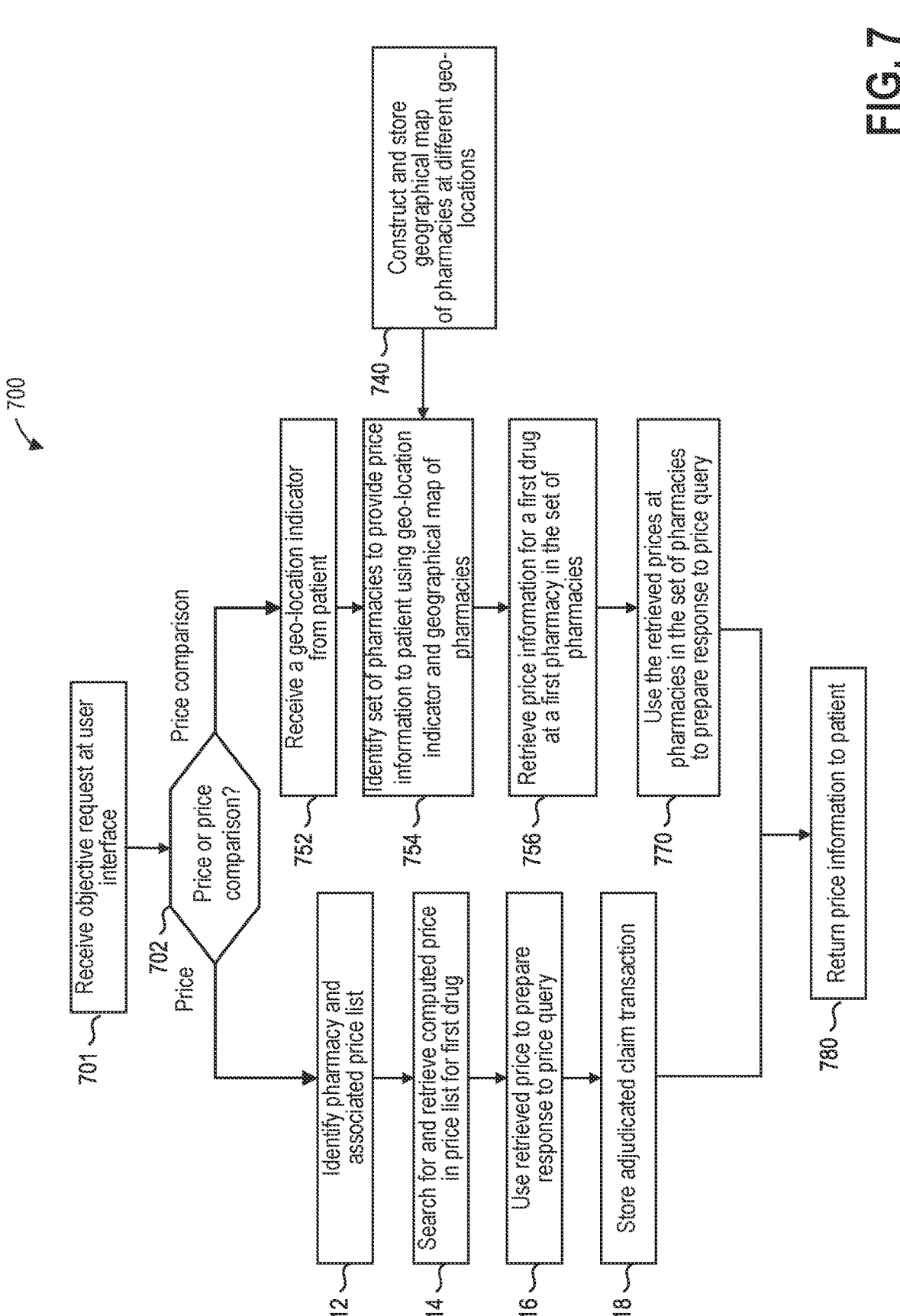
FIG. 7 illustrates a flow chart of an example method for a patient to send a price query for a product using the price determined by a system of the present disclosure or to send a price comparison query for a product at a set of pharmacies to retrieve computed or collected prices, according to one aspect of the present disclosure.

FIG. 7 illustrates a flow chart of an example method 700 for submission of a request for an objective, such as a price query or a price comparison, to a system, such as any of the systems 100, 200, 300, 1600, and 1700 of FIGS. 1-3, and 16-17, to obtain an output value, according to at least one embodiment of the present disclosure. The objective may be submitted by a patient at a patient user interface provided by the system (e.g., the patient user interface 186 of FIG. 1, the user interfaces 202 of FIG. 2, or the user interfaces 392 of FIG. 3) and received by one or more APIs implemented by the system. In at least one embodiment, the one or more APIs may be configured to receive drug prices from different customers (e.g., pharmacies) at different geographic locations and store the drug prices at a storage location such as a memory of the system.

At step 702, method 700 may include confirming if the requested objective is a price query or a price comparison query for a particular product, such as a drug. If the requested objective is a price query, method 700 may including proceeding to step 712 to identify a pharmacy corresponding to the price query as well as an associated price list. The pharmacy and the associated price list may be included with a plurality of inputs to the system or may be stored at a database of the system. At step 714, method 700 may include searching for and retrieving a price based on the pharmacy. In at least one embodiment, the price may be retrieved from the associated price list. In at least one other embodiment, the price may be computed in real-time by one or more ML models of the system and retrieved from the one or more ML models.

At step 716, method 700 may include using the retrieved price to prepare a response to the price query, which may include adjudicating a claim. Method 700 may then include storing an adjudicated claim transaction at a memory of the system at step 718. At step 780, method 700 may including returning information regarding the price to the patient. For example, the information may be displayed at the patient user interface.

Returning to step 702, if the requested objective is a price comparison query, method 700 may include, at step 752, receiving a geo-location indicator from the patient via the patient user interface. The geo-location indicator may be used in conjunction with a stored geographical map of available pharmacies, at step 754, to identify a set of pharmacies from which price information may be used to provide information to the patient. In at least one embodiment, the geographical map may be constructed, at step 740, using a component of the system, such as KG structures (e.g., the KG structures 252 of FIG. 2) to generate the geographical map. The geographical map may be stored at the memory of the system. At step 756, method 700 may include retrieving price information for a drug at pharmacy selected from the set of pharmacies. Retrieving the price information may include retrieving the more than one price from a price list of the pharmacy or from one or more ML models trained to estimate drug prices.

At step 770, method 700 may include using the retrieved prices from the pharmacy to prepare a response to the price comparison query. Method 700 may include proceeding to step 780, as described above to return the price information to the patient at the patient user interface.

FIG. 8 illustrates a flow chart of an example method 800 for clustering items in item cluster, such as drugs in drug clusters, according to at least one embodiment of the present disclosure. The drug clusters may, for example be used to estimate, recommend, and/or determine return values and/or information in response to requested objectives submitted to a system, such as any of the systems 100, 200, 300, 1600, and 1700 of FIGS. 1-3, and 16-17. At step 801, method 800 may include receiving a customer identifier. In at least one embodiment, the customer identifier may be received by one or more APIs of the system from a customer through a customer user interface (e.g., the customer user interface 132 of FIG. 1, the user interfaces 202 of FIG. 2, or the user interfaces 392 of FIG. 3).

At step 810, method 800 may include identifying a customer and other incoming information including one or more of a plurality of inputs, such as ML models to be used, a price list, and KG structures to be used as entered by the customer. Method 800 may further include receiving, at step 812, at least a set of drug clustering criteria for the identified customer, e.g., from the customer via the customer user interface. The incoming information may input to one or more ML models at step 820. In at least one embodiment, at least one of the one or more ML models included in drug clustering module, such as the second ML model 234 of the drug clustering module 232 of FIG. 2. The ML model may use the incoming information, including the drug clustering criteria, to group drugs in cluster in a drug list and output the drug clusters at step 825.

At step 830, method 800 may include associating one or more other ML models with each drug cluster. The other ML models may include at least one ML model included in a ML pricing module that is trained to estimate, recommend, and/or determine drug prices, such as the first ML model 212 of the ML pricing module 210 of FIG. 2. At step 840, method 800 may include using each of the other ML models associated with the drug clusters to compute a price of one or more drugs for each drug cluster following a process such as method 400 of FIG. 4.

Figure 9:
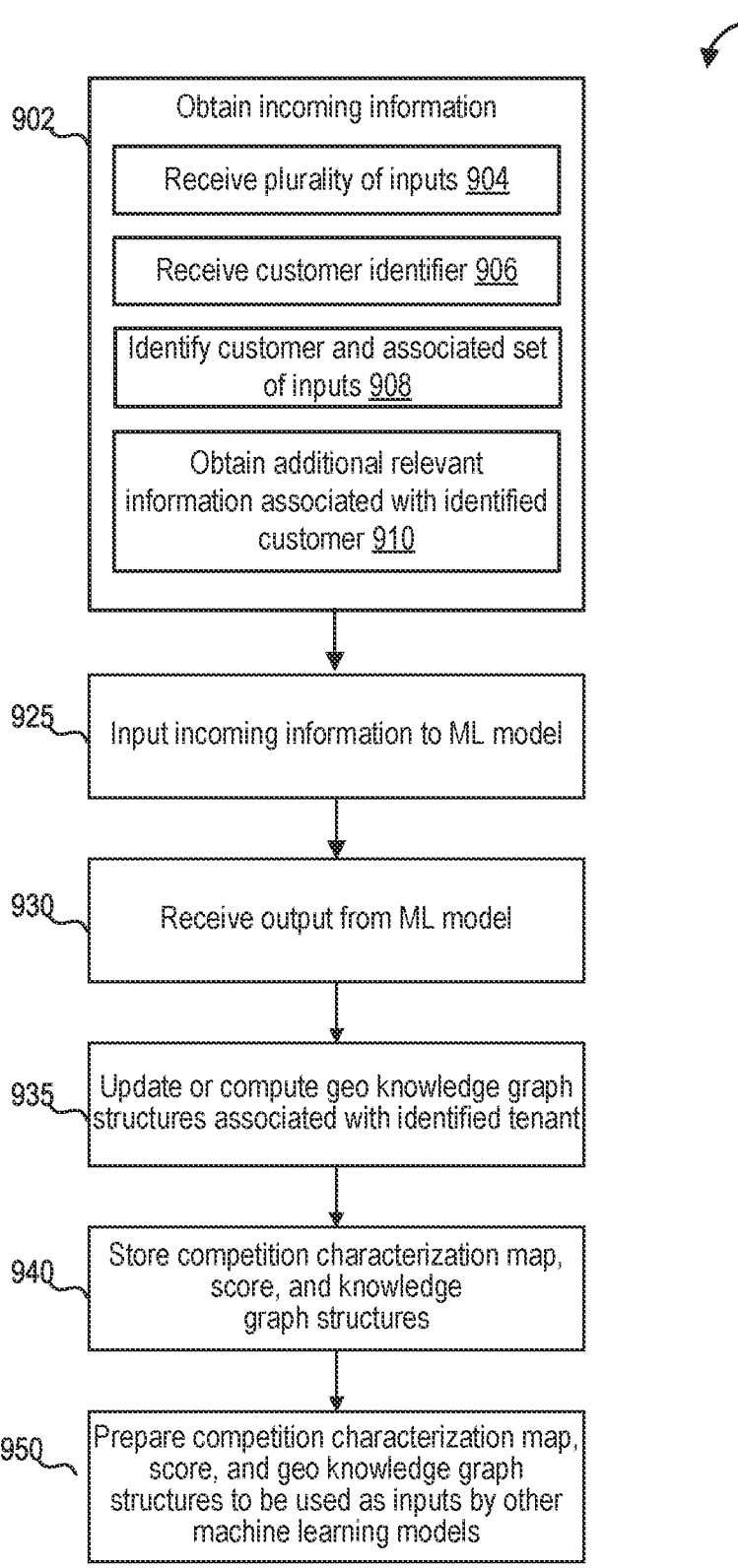
FIG. 9 illustrates a flow chart of an example method for computing a competition characterization map or a score, or for computing or updating a geo knowledge graph structures for a first customer, according to one aspect of the present disclosure.

FIG. 9 illustrates a flow chart of an example method 900 for generating and returning competition information at a system, such as any of the systems 100, 200, 300, 1600, and 1700 of FIGS. 1-3, and 16-17, according to at least one embodiment of the present disclosure. In at least one embodiment, the competition information may be used to provide a response to a requested objective input to the system, such as a request to obtain a drug price or drug comparison. The competition information may include a characterization map with a list of competitive pharmacies or geographical KG structures for a customer or a characterization score. As an example, the characterization map may be a collection of data that show relationships between selected inputs of a plurality of inputs and drug prices. For example, the characterization map may show statistical averages for drug prices according to geographic location. Similarly, the characterization score may be statistical information indicating a relationship between a specific input of a plurality of inputs and drug price.

At step 902, method 900 may include obtaining incoming information. In at least one embodiment, obtaining incoming information may include receiving at least a portion of the incoming information entered by a customer at a customer user interface (e.g., the customer user interface 132 of FIG. 1, the user interfaces 202 of FIG. 2, or the user interfaces 392 of FIG. 3). Obtaining the incoming information may include, for example, receiving a plurality of inputs at step 904 and a customer identifier at step 906 at one or more APIs of the system. Obtaining the incoming information may further include, at step 908, identifying the customer from the customer and locating or selecting an associated set of inputs from one or more of the received plurality of inputs and additional inputs that may be stored at a memory of the system. At step 910, obtaining the incoming information may also include obtaining additional information relevant to the customer. The additional information may include geographical, demographic, and other information associated with the identified customer.

At step 925, method 900 may include inputting the incoming information to one or more ML models. In at least one embodiment, the one or more ML models may be trained to generate a characterization map or score and may be included in a competition characterization module of the system, such as the third ML model 238 of the competition characterization module 236 of FIG. 2. Method 900 may include receiving the competition characterization map or score output by the one or more ML models at step 930 and, at step 935, the output may be used to update or compute geographical KG structures associated with the identified customer. In at least one embodiment, the geographical KG structures may be stored at a memory of the system and generated by a KG structures component of the system, such as the KG structures 252 of FIG. 2.

At step 940, method 900 may include storing the competition characterization map or score and the updated KG structures, e.g., at the system memory. Method 900 may further include, at step 950, preparing the stored competition characterization map or score and the geographical KG structures to be used as inputs to other ML models. In at least one embodiment, the other ML models may include ML models trained to generate price estimations, recommendations, and/or determinations, such as the one or more ML models of method 400 and the first ML model 212 of the ML pricing module 210 of FIG. 2.

Figure 10:
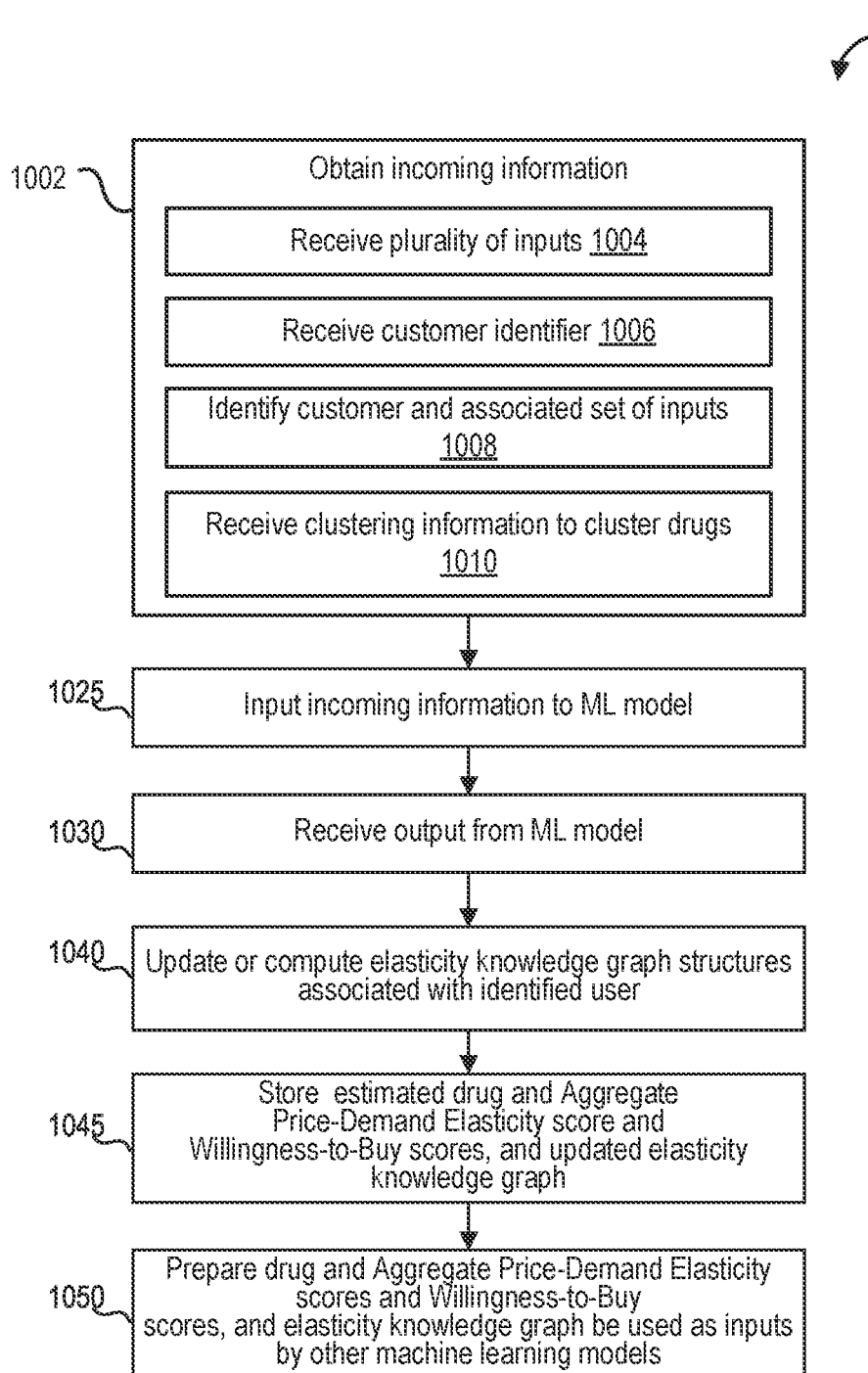
FIG. 10 illustrates a flow chart of an example method for estimating a Price/Demand Elasticity score and a Willingness to Buy score for a product and for estimating an Aggregate Price/Demand Elasticity score and an Aggregate Willingness to Buy score for a product cluster in a product list associated with a first customer, according to one aspect of the present disclosure.

FIG. 10 illustrates a flow chart of an example method 1000 for, using a system such as any of the systems 100, 200, 300, 1600, and 1700 of FIGS. 1-3, and 16-17, estimating parameter scores, including a Price/Demand Elasticity score, a Willingness to Buy (WTB) score for a drug, an Aggregate Price/Demand Elasticity score, and an Aggregate Willingness to Buy score, according to at least one embodiment of the present disclosure. The parameter scores may be obtained for a drug cluster in a drug list associated with a first customer according to one aspect of the present disclosure. In at least one embodiment, the drug cluster may be one or more drug clusters grouped based on an output from one or more ML models trained to cluster drugs, such as the second ML model 234 of the drug clustering module 232 of FIG. 2 and according to method 800 of FIG. 8.

At step 1002, method 1000 may include obtaining incoming information. In at least one embodiment, obtaining incoming information may include receiving at least a portion of the incoming information entered by a customer at a customer user interface (e.g., the customer user interface 132 of FIG. 1, the user interfaces 202 of FIG. 2, or the user interfaces 392 of FIG. 3). Obtaining the incoming information may include, for example, receiving a plurality of inputs at step 1004, which may include a requested objective, and a customer identifier at step 1006 at one or more APIs of the system. Obtaining the incoming information may further include, at step 1008, identifying the customer using the customer identifier and locating or selecting an associated set of inputs from one or more of the received plurality of inputs and additional inputs that may be stored at a memory of the system. At step 1010, obtaining the incoming information may also include obtaining clustering information indicating criteria for clustering or grouping drugs. For example, the clustering information may include one or more of class of drug, side effects of a drug, availability of a drug, manufacturer of a drug, shelf life of a drug, interactions of a drug with other drugs, etc.

At step 1025, method 1000 may include inputting the incoming information to one or more ML models of the system to obtain estimates of the parameters scores described above. In at least one embodiment, the one or more ML models may be trained to estimate the scores and may be included in a willingness to buy estimation module of the system, such as the fourth ML model 247 of the willing to buy estimation module 240 of FIG. 2. Method 1000 may also include receiving the estimated parameter scores as output by the one or more ML models at step 1030.

At step 1040, method 1000 may include using the output from the one or more ML models to update or compute elasticity KG structures associated with the identified customer. In at least one embodiment, the elasticity KG may be included in a KG structures component of the system, such as the KG structures 252 of FIG. 2. The parameter scores and the updated elasticity KG may be stored, e.g., in a memory of the system, at step 1045. At step 1050, method 1000 may include preparing the stored parameter scores and the elasticity KG to be used as inputs to one or more other ML models. In at least one embodiment, the other ML models may be the one or more ML models used to estimate, recommend and/or determine drug prices in method 400.

FIG. 11 illustrates a flow chart of an example method 1100 for, using a system such as any of the systems 100, 200, 300, 1600, and 1700 of FIGS. 1-3, and 16-17, returning a drug price and/or a drug recommendation customized for a requester, according to at least one embodiment of the present disclosure. The requester may be for example, one or more of a patient and a customer. Method 1100 may be performed in conjunction with method 400 to return an output value that is optimized according to specific criteria associated with the requester.

At step 1102, method 1100 may include obtaining incoming information. In at least one embodiment, obtaining incoming information may include receiving at least a portion of the incoming information entered by one or more of a patient at a patient user interface and a customer at a customer user interface (e.g., the patient user interface 186 and the customer user interface 132 of FIG. 1, the user interfaces 202 of FIG. 2, or the user interfaces 392 of FIG. 3). Obtaining the incoming information may include, for example, receiving a plurality of inputs at step 1104, which may include a requested objective such as a price query, a customer identifier at step 1106, a patient identifier at step 1108, patient specific information at step 1110, and patient clustering information at step 1112, at one or more APIs of the system. The patient-specific information may include medical history information, insurance benefit information, demographics information, lifestyle information, therapeutic information, or other information for the identified patient. The patient clustering information may include indications and/or criteria for how the patient-specific information may be grouped into patient clusters. Obtaining the incoming information may further include, at step 1114, assimilating the incoming information (e.g., the information received at steps 1104-1112). In at least one embodiment, assimilating the information may include one or more of processing, cleaning and identifying the plurality of inputs and the patient-specific information, which may include removing extraneous or irrelevant information, apportioning relevant and useful information into groups and recombining the information based on relationships among the information. Assimilating the information may also include using the customer identifier to identify a customer and select inputs from the plurality of inputs associated with the customer, ML models suitable to process the selected inputs, a price list, and/or KG structures relevant to the identified customer. Assimilating the information may further include using the patient identifier to identify a patient, and using the patient-specific information and the patient clustering information to assign the identified patient to a patient cluster.

At step 1140, the method 1100 may include inputting portions of the incoming information associated with the patient (e.g., the patient-specific information, the patient clustering information, and the cluster to which the patient is assigned) to one or more ML models. In at least one embodiment, the one or more ML models may be trained to cluster the patient with patients of similar characteristics and assign the corresponding cluster-specific information to the patient. The one or more ML models may, for example, be similar to the fifth ML model 224 of the ML pricing personalization module 222 of FIG. 2. An output from the one or more ML models may be received at step 1142, where the output may include estimated additional patient-specific information such as the cluster-specific information described above, and stored at step 1144, at a memory of the system.

At step 1146, the stored estimated additional patient-specific information may be input to additional ML models along with the incoming information from step 1102. The additional ML models may include one or more of a first additional ML model trained to estimate, recommend, and/or determine the price of a drug and a second additional ML model trained to recommend one or more of benefit vs. cash payment comparisons, alternative drugs, and personalized therapeutic information to the identified patient. In at least one embodiment, the first additional ML model may use the patient-specific information in addition to the plurality of inputs used to obtain a drug price in method 400. In at least one embodiment, the first additional ML model may be similar to the sixth ML model 226 Of the ML pricing personalization module 222 of FIG. 2. In at least one embodiment, the second additional ML model may be similar to the seventh ML model 230 of the ML recommendation module 228 of FIG. 2.

At step 1148, method 1100 includes receiving outputs from the additional ML models and storing the outputs at the memory of the system at step 1150. In at least one embodiment, the output include one or more of a patient-specific price and patient-specific recommendations. At step 1152, the output is returned to the requester by displaying the output at the patient and/or customer user interface.

Figure 12:
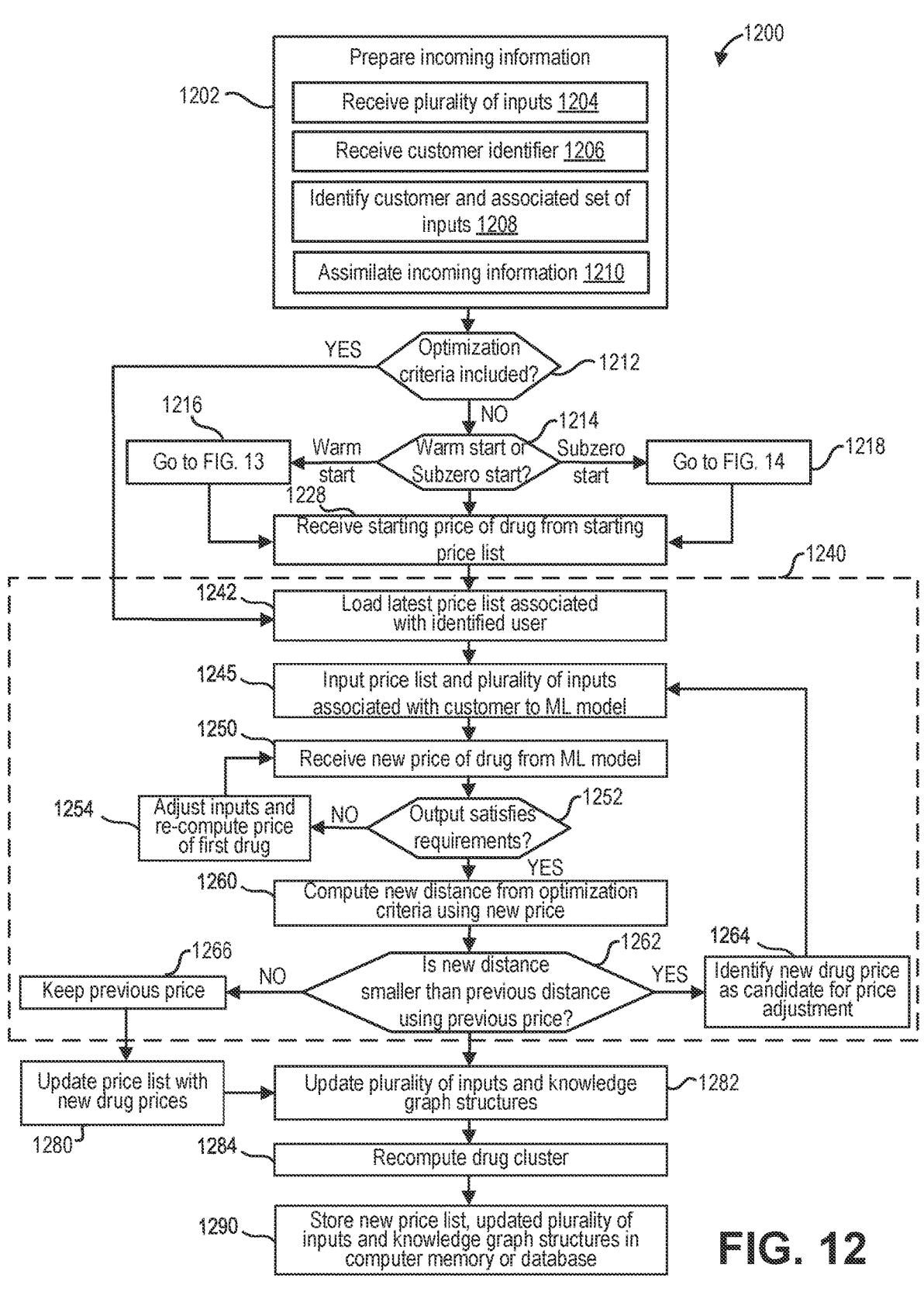
FIG. 12 illustrates a flow chart of an example method for iteratively estimating, recommending, or determining the optimal price for one or more products in a product list for a customer, according to one aspect of the present disclosure.

FIG. 12 illustrates a flow chart of an example method 1200 to be performed by a system, such any of the systems 100, 200, and 300 of FIG. 1-3, for iteratively estimating, recommending, and/or determining a target value or set of values for an item or a set of items, such as an optimal price for one or more drugs in a drug list for a customer, according to at least one embodiment of the present disclosure. According to another embodiment of the present disclosure, method 1200 may be a process for iteratively determining an optimal price for at least a drug in a drug list according to at least one optimization criteria for a customer in a set of customers. Method 1200 may include steps that are iterated, with each iteration occurring at a configurable, regular frequency, or occurring as triggered by a certain event. For example, at each iteration, method 1200 may include re-computing prices and identifying a set of recommended price changes that are close to the optimization criteria. Method 1200 may further include updating inputs and re-computing drug clusters until the next iteration is triggered. In at least one embodiment, method 1200 as well as methods 1300 and 1400, which are optional process to be used in conjunction with method 1200, may be performed in conjunction with or in place of method 400 of FIG. 4.

At step 1202, method 1200 may include preparing incoming information, which may, in at least one embodiment, be received from a requester, such as a customer or a patient. In at least one embodiment, at least a portion of the incoming information may be entered by the customer or the patient at a user interface (e.g., the patient user interface 186 and the customer user interface 132 of FIG. 1, the user interfaces 202 of FIG. 2, or the user interfaces 392 of FIG. 3). Preparing the incoming information may include, for example, receiving a plurality of inputs at step 1204, which may include a requested objective such as an optimized price query and a customer identifier at step 1206 at one or more APIs of the system. Preparing the incoming information may further include, at step 1208, identifying the customer using the customer identifier, locating or selecting an associated set of inputs from the plurality of inputs, identifying one or more ML models to be used to process the incoming information, as well as locating and/or selecting one or more relevant price lists and one or more KG structures that may be stored at a memory of the system. Preparing the incoming information may also include, at step 1210, assimilating the received, selected, and/or located incoming information. In at least one embodiment, assimilating the information may include one or more of processing, cleaning and identifying the plurality of inputs and the patient-specific information, which may include removing extraneous or irrelevant information, apportioning relevant and useful information into groups and recombining the information based on relationships among the information.

At step 1212, method 1200 may include confirming if one or more optimization criteria are included in the incoming information. In at least one embodiment, the optimization criteria may be included in the plurality of inputs entered by the requester and may be criteria indicating how a response to the objective request may be optimized. In at least one embodiment the optimization criteria may be used to determine an initial starting value of an item, such as starting price and/or a starting price list corresponding to the identified customer that considers the optimization criteria. If the optimization criteria are included, method 1200 may include proceeding to step 1242, described further below. If the optimization criteria are not included, method 1200 may include continuing to step 1214 to confirm if a Warm start or a Subzero start is indicated. In at least one embodiment, the Warm start or the Subzero start may be used to obtain optimization criteria when optimization criteria are not included in the incoming information.

In at least one embodiment, the Warm start may be a process for estimating, recommending, and/or determining an initial starting value, such as a starting price of a drug where information regarding historical claim transactions for the drug is available and the Subzero start may be a process for estimating, recommending, and/or determining a starting price of a drug where information regarding historical claim transactions for the drug is not available. If the Warm start is indicated, method 1200 may proceed to perform a process described further below with reference to FIG. 13 and if the Subzero start is indicated, method 1200 may instead proceed to perform a process described further below with reference to FIG. 14. After either process is carried out, method 1200 may include, at step 1228, receiving a starting price of a drug from a starting price list as obtained via one of the processes of FIGS. 13 and 14.

Method 1200 may include proceeding to step 1242 which may be an iterative portion of method 1220, as indicated by dashed box 1240. The iterative portion may include steps 1242-1266 and one or more of the steps included therein may be iterated until a desired outcome is obtained. In at least one embodiment, by iterating one or more steps of the iterative portion, one or more drug prices may be obtained that are optimized according to the optimization criteria.

At step 1242, method 1200 may include loading a most recent price list associated with the identified customer and a drug indicated by the incoming information. In at least one embodiment, the most recent price list may be obtained based on optimization criteria identified from the plurality of inputs or from performing one of the Warm start or the Subzero start. The price list may be input, at step 1245, to one or more ML models to obtain an estimation, recommendation, and/or determination of a new price of the drug output by the one or more ML models at step 1250. In at least one embodiment, the one or more ML models may be the one or more ML models used in method 400 to obtain a drug price. For example, the one or more ML models may be similar to the first ML model 212 of the ML pricing module 210 of FIG. 2.

At step 1252, method 1200 may include confirming if the drug price output by the one or more ML models satisfies requirements indicated by the incoming information at step 1252. In at least one embodiment, the requirements may include policies and constraints indicated by the optimization criteria. If the output does not satisfy the requirements, method 1200 may include continuing to step 1254 to adjust at least a portion of the inputs of the plurality of inputs and to re-compute the drug price. For example, one or more parameters used to compute the drug price may be adjusted. Method 1200 may then include returning to step 1245 to input the price list and adjusted inputs to the one or more ML models. If the output satisfies the requirements at step 1252, method 1200 may include proceeding to step 1260 to compute a new distance from the optimization criteria using the output drug price. In at least one embodiment, a distance between, for example a drug price and the optimization criteria may be a difference by which the drug price differs from a drug price indicated by the optimization criteria.

At step 1262, method 1200 may include confirming if the computed new distance is smaller than the previous distance computed using a previous drug price. If the new distance is smaller, method 1200 may include proceeding to step 1264 to identify a new candidate drug price for price adjustment. For example, the new candidate drug price may be selected from the price list based on relevancy. Method 1200 may then include returning to step 1245 to input the new drug price to the one or more ML models.

If the computed new distance is not smaller than the previous distance at step 1262, method 1200 may include continuing to step 1266 to discard the new drug price and use the previous drug price to update the price list at step 1280. In at least one embodiment, the iterative portion of method 1200 may output more than one drug price for updating the price list. At 1282, method 1200 may include updating the plurality of inputs and the KG structures using the updated price list. Further, at step 1284, a drug cluster may be recomputed using the updated plurality of input and KG structures. For example, one or more ML models trained to infer drug clusters may be used to output new drug cluster based on the updated information. At 1290, method 1200 may include storing the new price list, updated plurality of inputs, and KG structures at a memory and/or database of the system.

Figure 13:
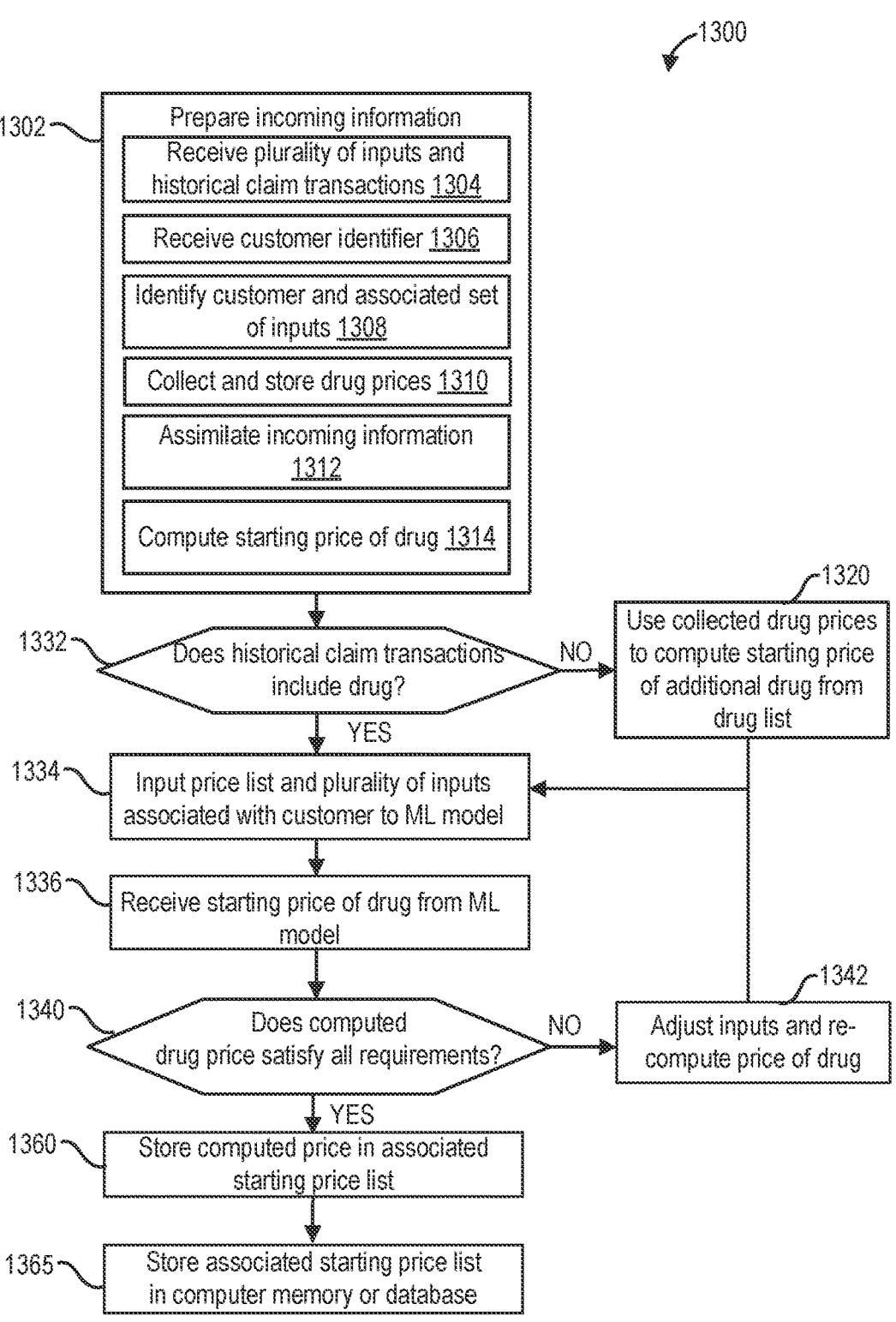
FIG. 13 illustrates a flow chart of an example method for estimating, recommending, or determining a starting price for one or more products for Warm Start according to the example method of FIG. 12, according to one aspect of the present disclosure.

FIG. 13 illustrates a flow chart of an example method 1300 for estimating, recommending, and/or determining the starting price for one or more drugs for a Warm Start to be used according to, for example, method 1200 of FIG. 12. In at least one embodiment, method 1300 may be performed by a Warm start module of the system, such as the Warm start module 216 of the ML pricing optimization module 214 of FIG. 2. At 1302, method 1300 may include preparing incoming information, which may, in at least one embodiment, be received from a requester, such as a customer or a patient. In at least one embodiment, at least a portion of the incoming information may be entered by the customer or the patient at a user interface (e.g., the patient user interface 186 and the customer user interface 132 of FIG. 1, the user interfaces 202 of FIG. 2, or the user interfaces 392 of FIG. 3). Preparing the incoming information may include, for example, receiving a plurality of inputs at step 1304, which may include a requested objective such as a starting drug price, and a customer identifier at step 1306 at one or more APIs of the system. Preparing the incoming information may further include, at step 1308, identifying the customer using the customer identifier, locating or selecting an associated set of inputs from the plurality of inputs, identifying one or more ML models to be used to process the incoming information, as well as locating and/or selecting one or more associated starting price lists and one or more KG structures that may be stored at a memory of the system. At step 1310, preparing the incoming information may include collecting and storing drug prices, e.g., in a drug list, for a drug at different pharmacies and geographic locations. Preparing the incoming information may also include, at step 1312, assimilating the received, selected, and/or located incoming information. In at least one embodiment, assimilating the information may include one or more of processing, cleaning and identifying the plurality of inputs and the patient-specific information, which may include removing extraneous or irrelevant information, apportioning relevant and useful information into groups and recombining the information based on relationships among the information. Preparing the incoming information may also include computing starting price of a drug from an associated starting price list at step 1314.

At step 1332, method 1300 may include confirming if the historical claim transactions include the drug. If the drug is not included, method 1300 may include proceeding to step 1320 to use the drug prices collected at step 1310 to compute a starting price of an additional drug from the associated starting price list. Method 1300 may then continue to step 1334, described below.

If the historical claim transactions include the drug, method 1300 may include inputting one or more of the associated starting price lists (or the computed starting prices of the drug and the additional drug when the drug is not included in the historical claim transactions) to one or more ML models trained to estimate, recommend, and/or determine a drug price. For example, the one or more ML models may be similar to the first ML model 212 of the ML pricing module 210 of FIG. 2. Method 1300 may include receiving an inferred starting price of the drug output from the one or more ML models at step 1336. At step 1340, method 1300 may include confirming if the computed starting drug price satisfies all requirements. In at least one embodiment, the requirements may include policies and constraints indicated by the plurality of inputs. If the requirements are not satisfied, method 1300 may include adjusting the plurality of inputs that are input to the one or more ML models at step 1342 and re-computing the starting price by inputting the adjusted plurality of inputs to the one or more ML models at step 1334. In at least one embodiment, the requirements may not be satisfied if additional prices for additional drugs are to be obtained.

If the requirements are satisfied, method 1300 may include continuing to 1360 to update the associated starting price list with one or more computed starting drug prices output by the one or more ML models. The updated associated price list may be stored at the memory or database of the system.

Figure 14:
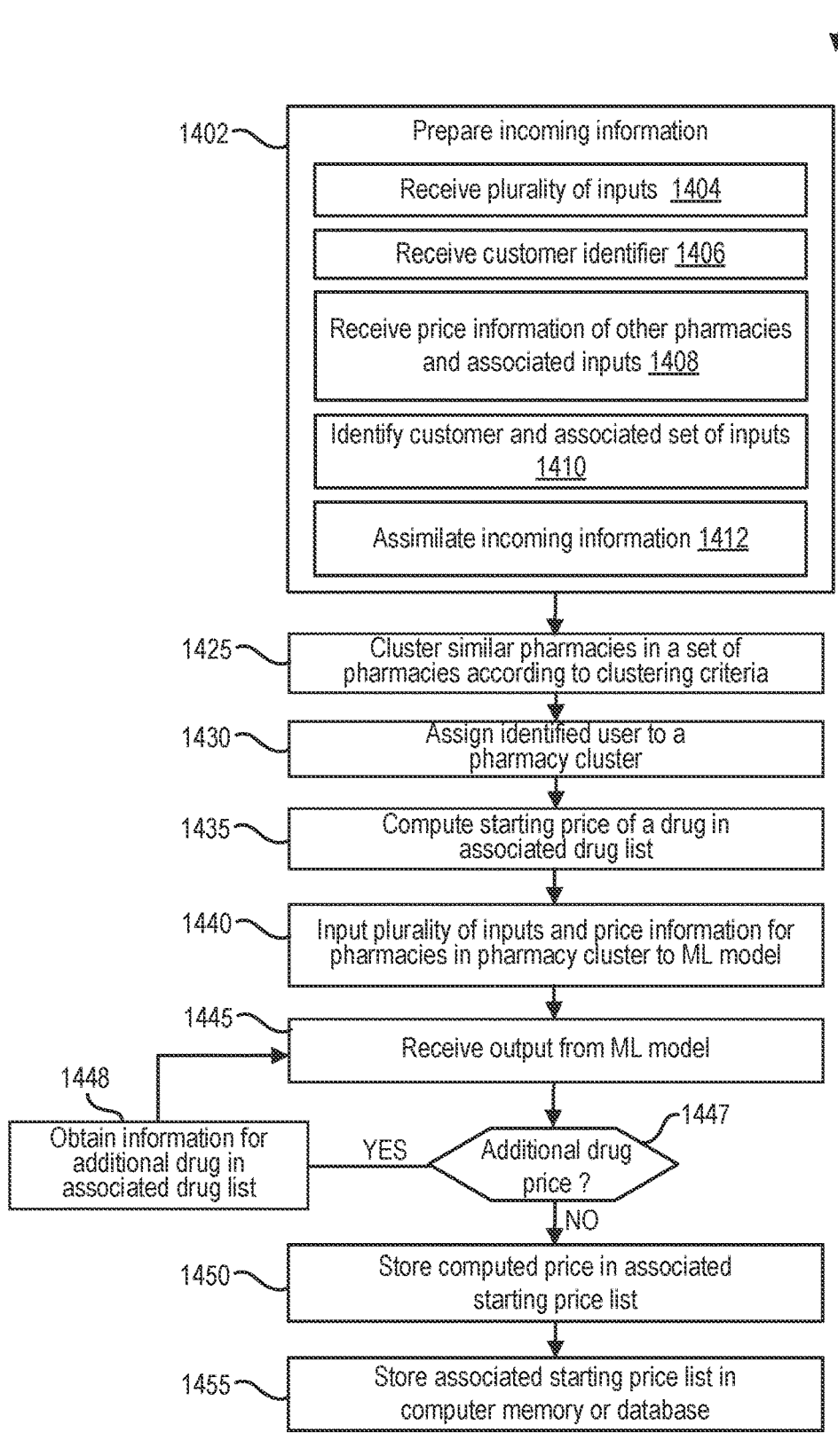
FIG. 14 illustrates a flow chart of an example method for estimating, recommending, or determining the starting price for one or more products for Subzero Start according to the example method of FIG. 12, according to one aspect of the present disclosure.

FIG. 14 illustrates a flow chart of an example method 1400 for estimating, recommending, and/or determining the starting price for one or more drugs for a Subzero start to be used according to, for example, method 1200 of FIG. 12. In at least one embodiment, method 1300 may be performed by a Subzero start module of the system, such as the Subzero start module 218 of the ML pricing optimization module 214 of FIG. 2. At 1402, method 1400 may include preparing incoming information, which may, in at least one embodiment, be received from a requester, such as a customer or a patient. In at least one embodiment, at least a portion of the incoming information may be entered by the customer or the patient at a user interface (e.g., the patient user interface 186 and the customer user interface 132 of FIG. 1, the user interfaces 202 of FIG. 2, or the user interfaces 392 of FIG. 3). Preparing the incoming information may include, for example, receiving a plurality of inputs at step 1404, which may include a requested objective such as a starting drug price, a customer identifier at step 1406, price information related to other customers (e.g., pharmacies) in a set of pharmacies along with associated input at step 1408, one or more associated starting price lists, one or more associated drug lists, and clustering criteria for grouping pharmacies in the set of pharmacies at one or more APIs of the system. Preparing the incoming information may further include, at step 1410, identifying the customer using the customer identifier, locating or selecting an associated set of inputs from the plurality of inputs, identifying one or more ML models to be used to process the incoming information, as well as locating and/or selecting one or more associated starting price lists and one or more KG structures that may be stored at a memory of the system. Preparing the incoming information may also include, at step 1412, assimilating the received, selected, and/or located incoming information. In at least one embodiment, assimilating the information may include one or more of processing, cleaning and identifying the plurality of inputs and the patient-specific information, which may include removing extraneous or irrelevant information, apportioning relevant and useful information into groups and recombining the information based on relationships among the information.

At step 1425, method 1400 may include clustering similar pharmacies included in the set of pharmacies based on the clustering criteria. By clustering users (e.g., pharmacies), the users may be grouped according to shared parameters (e.g., similarities) that may be indicated by the clustering criteria.

Similarities between the pharmacies may be determined based on parameters including, but not limited to, geographic location, size, number of clients, client demographics, etc. The identified customer may be assigned, at step 1430 to at least one of the pharmacy clusters based on a comparison of inputs of the plurality of inputs that are associated of the identified customer to inputs that are associated with the pharmacy cluster. Method 1400 may also include computing a starting price of a drug using an associated starting price list at step 1435.

At step 1440, method 1400 may include inputting the plurality of inputs and price information corresponding to pharmacies within the pharmacy cluster assigned to which the identified customer is assigned to one or more ML models. In at least one embodiment, the one or more ML models may be trained to estimate, recommend, and/or determine a starting price of a drug. For example, the one or more ML models may be similar to the eighth ML model 220 of the ML pricing optimization module 214 of FIG. 2. An output from the one or more ML models providing an inferred starting price of the drug may be received at step 1445.

At step 1447, method 1400 may include confirming if an additional drug price is desired. The additional drug price may be desired to obtain a starting price for another drug in an associated drug list. If another drug price is desired, method 1400 may include proceeding to 1448 to obtain information (e.g., selected input from the plurality of inputs) for an additional drug and return to step 1440 to input the information to the one or more ML models. If the additional drug price is not desired, method 1400 may include continuing to step 1450 to update the associated starting price list with the one or more computed starting drug prices and store the updated starting price list at a memory or database of the system.

Figure 15:
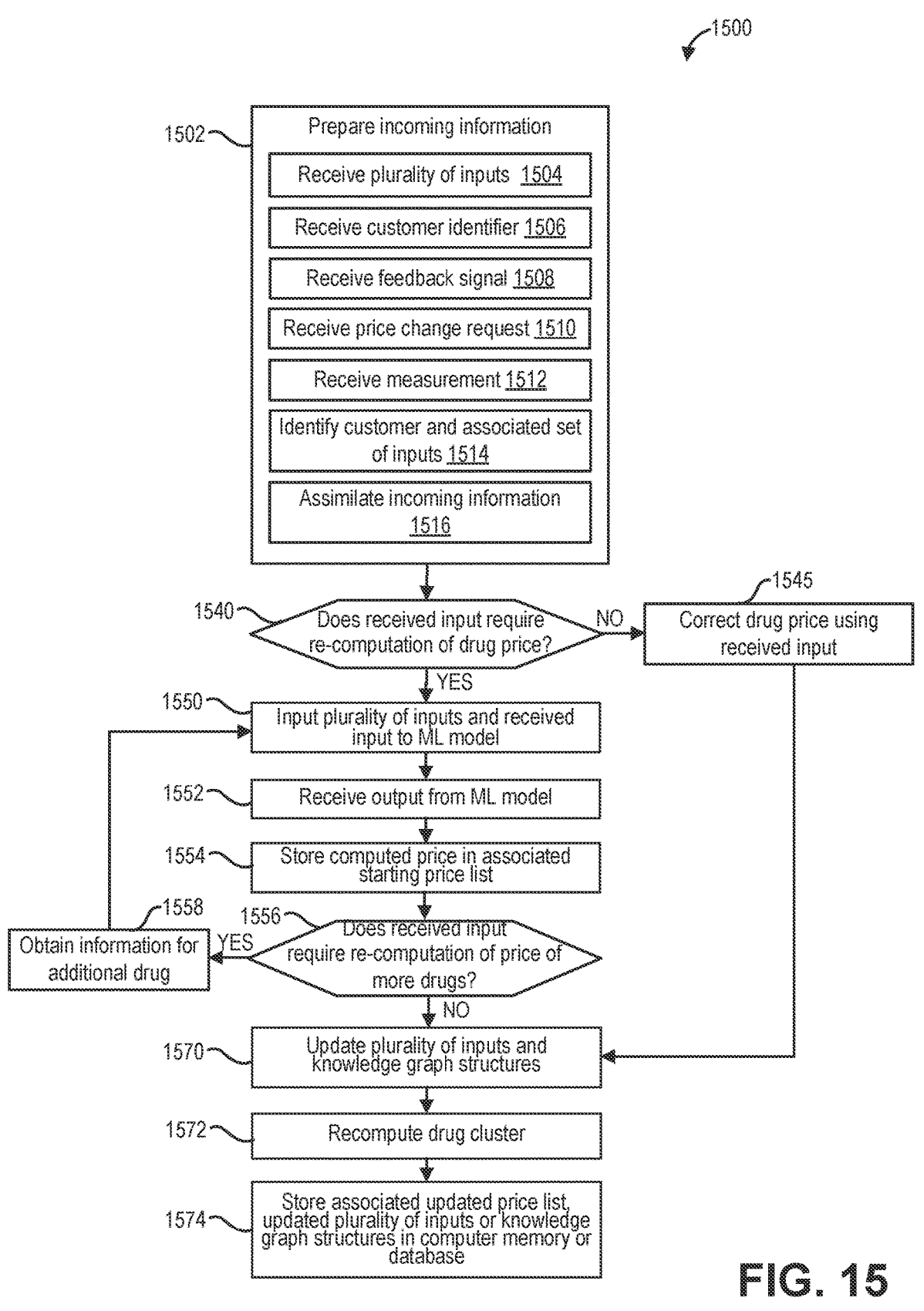
FIG. 15 illustrates a flow chart of an example method for a system of the present disclosure to receive a feedback input, a price change request, or a measurement to correct one or more product prices, according to one aspect of the present disclosure.

FIG. 15 illustrates a flow chart of an example method 1500 for a system, such as any of the systems 100, 200, 300, 1600, and 1700 of FIGS. 1-3, and 16-17, to correct one or more drug prices, according to at least one embodiment of the present disclosure. Method 1500, in at least one embodiment, may be performed in conjunction with a process for obtaining a drug price, such as method 400 of FIG. 4, as well as with any of the methods described herein. At 1502, method 1500 may include preparing incoming information, which may, in at least one embodiment, be received from a requester, such as a customer or a patient. In at least one embodiment, at least a portion of the incoming information may be entered by the customer or the patient at a user interface (e.g., the patient user interface 186 and the customer user interface 132 of FIG. 1, the user interfaces 202 of FIG. 2, or the user interfaces 392 of FIG. 3). Preparing the incoming information may include, for example, receiving a plurality of inputs at step 1504, which may include a requested objective such as a starting drug price, and receiving a customer identifier at step 1506. Preparing the incoming information may further include receiving additional inputs, including one or more feedback signals at step 1508, one or more price change requests at step 1510, and one or more measurements at step 1512. In at least one embodiment, the one or more feedback signals may be obtained from a feedback processing module, such as the feedback processing module 246 of the ML feedback loop module 244 of FIG. 2, and the one or more measurements may be obtained from a measurement module, such as the measurement module 250 of the ML feedback loop module 244 of FIG. 2, used to process information from one or more ML models (such as the one or more ML models of used for method 400). In at least one embodiment, the price change request may be received from the requester. Preparing the incoming information may further include, at step 1514, identifying the customer using the customer identifier, locating or selecting an associated set of inputs from the plurality of inputs, identifying one or more ML models to be used to process the incoming information, as well as locating and/or selecting one or more associated starting price lists and one or more KG structures that may be stored at a memory of the system. Preparing the incoming information may also include, at step 1516, assimilating the received, selected, and/or located incoming information. In at least one embodiment, assimilating the information may include one or more of processing, cleaning and identifying the plurality of inputs and the patient-specific information, which may include removing extraneous or irrelevant information, apportioning relevant and useful information into groups and recombining the information based on relationships among the information.

At step 1540, method 1400 may include confirming if the incoming information indicates the re-computation of a drug price is desired. In at least one embodiment, this may be determined based on the price change request received at step 1510. If the price change request indicates that a re-computation is not desired, method 1500 may include proceeding to step 1545 to correct the drug price using the incoming information. Method 1500 then may include continuing to step 1570, described further below.

If the re-computation is desired, method 1500 may include continuing to step 1550 to input the plurality of inputs and additional received input from the incoming information to one or more ML models. In at least one embodiment, the one or more ML models may be trained to estimate, recommend, and/or determine a drug price. For example, the one or more ML models may be similar to the first ML model 212 of the ML pricing module 210 of FIG. 2. A drug price output by the one or more ML models may be received at step 1552.

At step 1556, method 1500 may include confirming if the received input (e.g., the feedback signal, the price change request, and the measurement) indicate that re-computation of one or more additional drugs is desired. If re-computation is indicated, method 1500 may include proceeding to step 1558 to obtain information for the one or more additional drugs from the incoming information. Method 1500 may then include returning to step 1550 to input the information to the one or more ML models. If re-computation is not indicated at step 1556, method 1500 may include continuing to step 1570 to update the plurality of inputs and the KG structures. Method 1500 may further include re-computing one or more drug clusters based on the updated plurality of inputs and KG structures at step 1572. In at least one embodiment, the drug clusters may be output by one or more ML models of a drug clustering module, such as the second ML model 234 of the drug clustering module 232 of FIG. 2. At step 1574, method 1500 may include storing a price list that is updated based on the re-computed drug prices, the updated plurality of inputs, and the updated KG structures at a memory or database of the system.

Figure 16:
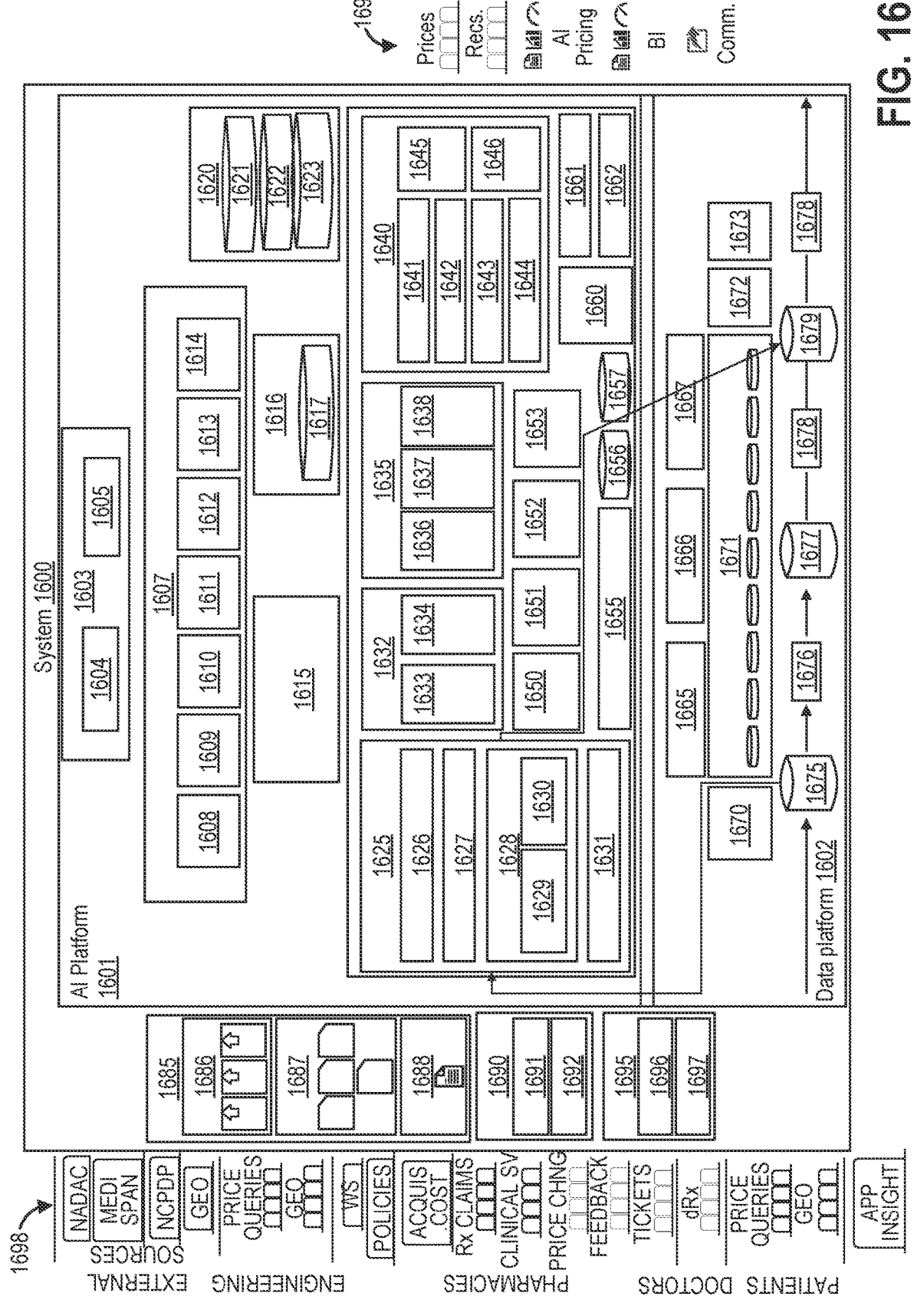
FIG. 16 illustrates a block diagram of an example embodiment of a system implementing the techniques of the present disclosure.

FIG. 16 illustrates a block diagram of an example embodiment of a system 1600 that may be used to implement the methods described herein. In at least one embodiment, system 1600 may be implemented at a computing device, such as a computing device 1800 of FIG. 18, described further below, in conjunction with systems 100, 200, and 300 of FIGS. 1-3. Various components may be included in system 1600 by which system 1600 may perform the steps of methods 400-1500, such as an AI platform 1601, a data platform 1602, a customer facing secure user interfaces 1685, and a source control 1620, which may form main platforms of system 1600. The components may include various sub-components to interface (e.g., communicate) with one another and exchange data.

In at least one embodiment, the AI platform 1601 may include sub-components for training and deploying ML models, e.g., the ML models depicted in FIG. 2, such as an AI lifecycle orchestration and monitoring module 1603, which may utilize an AI life cycle monitoring center (LCMC) 1604, an AI life cycle orchestrator App (LCO APP) 1605. Another sub-component of the AI platform 1601 may include AI and data internal microservices 1607, which may include a price list generation and management service 1608, a pre-analysis management service 1609, a competitive price scrapings service 1610, a price query management service 1611, a price change request management service 1612, a feedback loop management service 1613, and a testing and auditing service 1614. The sub-components of the AI platform 1601 may further include AI models 1615, KG and graph neural networks 1616, which may include a KG database 1617, and a source control 1620, which may include a staging Git databases 1621, 1622, and a product Git database 1623.

In at least one embodiment, an automated AI data pipelines 1625 sub-component of the AI platform 1601 may include an AI batch data preparation pipeline 1626, an AI featurization pipeline 1627, a stream AI data processing pipeline 1628, which may further include an AI real time data preparation pipeline 1629, and an event handling module 1630, and an AI data labeling pipeline 1631. A model development and training pipeline 1632 of the AI platform 1601 may include a tracking server module 1633 and an auto logging module 1634, and a CI/CD pipeline 1635 may include a unit testing (CI) module 1636, an integration testing (CI) module 1637, and a CD module 1638. A model deployment pipeline 1640 sub-component of the AI platform 1601 may include a model registry module 1641, a model serving module 1642, AI batch or streaming inferencing 1643, a monitoring module 1644, a reinforced learning module 1645, and a feedback loop module 1646.

In at least one embodiment, the AI platform 1601 may further include additional sub-components such as a tables pipeline 1650, a pipeline builder module 1651, hyperparameter optimization 1652, a distributed training module 1653, AI libraries 1655, a model store 1656, a feature store 1657, a GPU optimization module 1660, clustering compute 1661, and compute 1662.

In at least one embodiment, the data platform 1602 may include various sub-components for managing data, such as a Lakehouse data management module 1665, a data governance model 1666, open APIs 1667, an AI and data workspace management module 1670, AI and data workspaces 1671, which provide include a workspace per customer, development workspaces 1672, and BI workspaces 1673. The data platform 1602 may further include a bronze database 1675, which may transmit data to the automated AI data pipelines 1625, BI ETLs 1676, a silver database 1677, ETLs 1678, and a gold database which may receive data from the automated AI data pipelines 1625.

In at least one embodiment, the customer facing secure user interfaces 1685 may include various sub-components for receiving and processing data input to system 1600 through user interfaces, such as the user interfaces 132, 186 of FIG. 1, the user interfaces 202 of FIG. 2, and the user interfaces 392 of FIG. 3. The sub-components may include structured data uploads 1686 for uploading pharmacy data, pharmacy policies, acquisition costs, and the like, data I/O with secure forms 1687, which may include forms for price change requests, tickets, feedback, and price checks, and real-time reports 1688.

In at least one embodiment, the sub-components of the customer facing secure user interfaces 1685 may further include APIs 1690, such as a quantity pricing API 1691 and a price checking Api 1692, and may include additional APIs which may used similarly to the plurality of APIs 122 of FIG. 1, the APIs 204 of FIG. 2, and the APIs 391 of FIG. 3. Further, the customer facing secure user interfaces 1685 may include more data I/O 1695, such as a batch data I/O 1696 and a stream data I/O 1697.

In at least one embodiment, system 1600 may be configured to receive a plurality of inputs 1698, from sources including, but not limited to, external sources providing NADAC, Medispan, NCPDP, and geographical data, engineering sources providing price queries and geographical data streams, pharmacies providing WS data, policy data, acquisition cost data, prescription claim data, clinical services data, price change request data, feedback loop streams, and ticket streams, doctors (e.g., clinicians) providing prescription data, and patients providing price query data, geographical data, as well as data from software applications insight. In at least one embodiment, system 1600 may be further configured to provide a plurality of outputs 1699 including, but not limited to, price data, recommendation data, AI-based pricing data such as ports, dashboards, and analytics, BI data such as reports, dashboards, and analytics, and communications.

Figure 17:
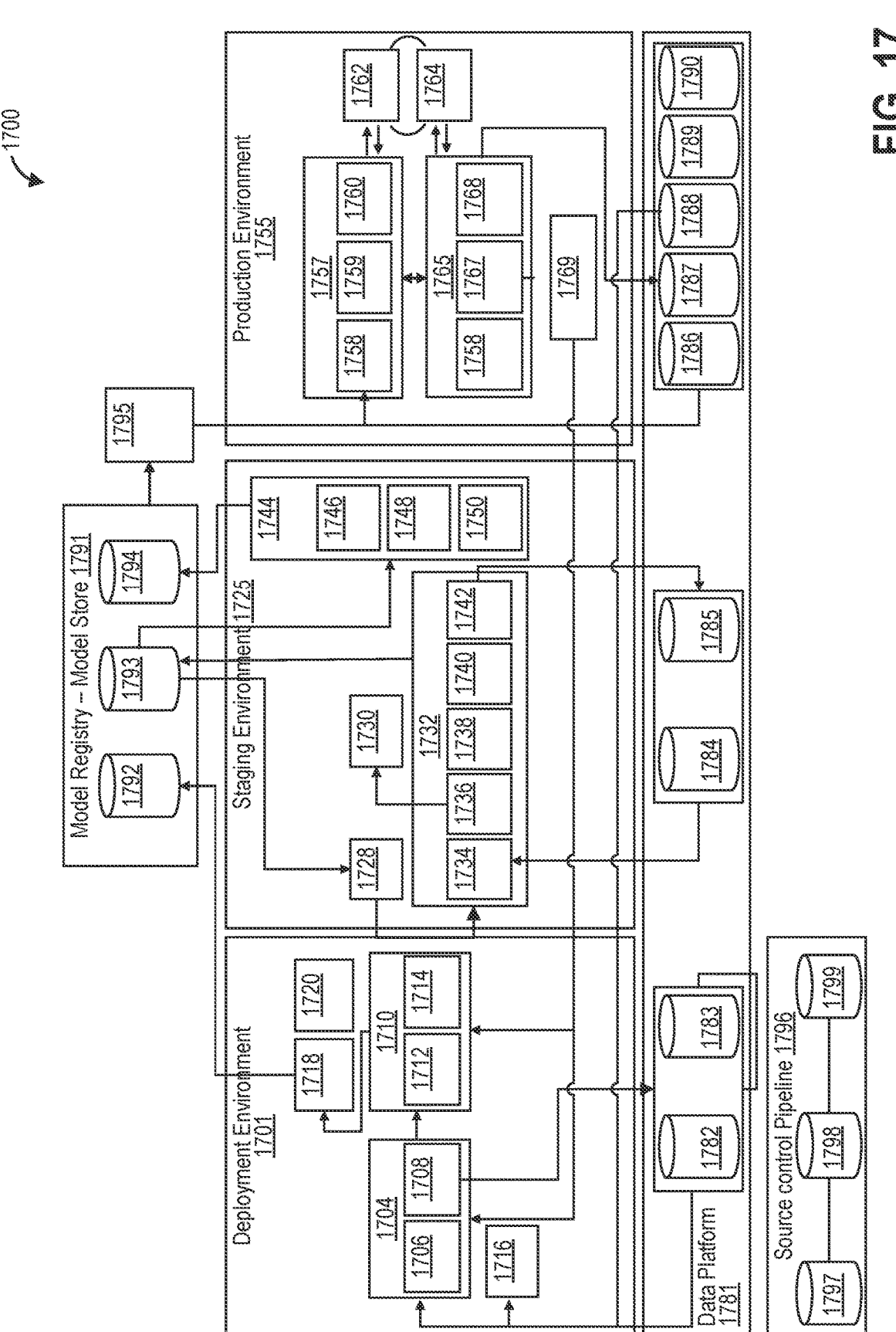
FIG. 17 illustrates a block diagram of another example embodiment of a system implementing the techniques of the present disclosure.

FIG. 17 illustrates a block diagram of an example embodiment of a system 1700 that may be used to implement the methods described herein. In at least one embodiment, system 1700 may be implemented at a computing device, such as a computing device 1800 of FIG. 18, described further below, in conjunction with systems 100, 200, 300, and 1600 of FIGS. 1-3 and 16. System 1700 may include various components including a development environment 1701, a staging environment 1725, a production environment 1755, a data platform 1781, a model registry/model store 1791, a model server module 1795, and a source control pipeline 1796. The components of system 1700 may be configured to exchange data as shown in FIG. 17 and described further below.

In at least one embodiment, the development environment 1701 may include sub-components such as a feature table refresh pipeline 1704, which may further include a data preparation module 1706 and a featurization module 1708, a data analysis module 1716, and a model training pipeline 1710, which may include a training and tuning module 1712 and an evaluation module 1714. Data from the model training pipeline 1710 may be fed to a tracking server module 1718 of the development environment 1701. The development environment 1701 may also include an auto logging module 1720.

In at least one embodiment, the staging environment 1725 may include sub-components such as a unit testing (CI) module 1728, a tracking server module 1730, an integration test (CI) pipeline 1732, and a continuous deployment (CD) pipeline 1744. The integration test (CI) pipeline 1732 may receive data from the development environment 1701, and may include a feature store test module 1734, a model training test module 1736, which may transmit data to the tracking server module 1730, a model deployment test module 1738, an inference test module 1740, and a model monitoring test module 1742. The CD pipeline 1744 may include a compliance checks module 1746, a compare staging versus production module 1748, and a model transition to production module 1750.

In at least one embodiment, the production environment 1755 may include sub-components such as a batch or streaming inference pipeline 1757, which may exchange data with a reinforced learning module 1762 and a model monitoring pipeline 1765. The reinforced learning module 1762 may further exchange data with a feedback loop module 1764, which may, in turn, exchange data with the model monitoring pipeline 1765. The batch or streaming inference pipeline 1757 may include a data ingest module 1758, a model inference module 1759, and a publish predictions module 1760 and the model monitoring pipeline 1765 may include a data ingest module 1766, a check model performance and data drift module 1767, and a publish metrics module 1768. The sub-components of the production environment 1755 may further include trigger model retraining or code change 1769, which may transmit data to the feature table refresh pipeline 1704 and the model training pipeline 1710.

In at least one embodiment, the data platform 1781 may include sub-components such as a development feature tables database 1782 and a development temporary tables database 1783 both of which may send data to the feature table refresh pipeline 1704 and the data analysis module 1716 and receive data from the featurization module 1708. The sub-components of the data platform 1781 may also include a staging feature tables database 1784 and a staging temporary tables database 1785, both of which may send data to the feature store test module 1734 and receive data from the model monitoring test module 1742. The sub-components of the data platform 1781 may further include a set of databases including a production feature tables database 1786, a production monitoring tables database 1787, a production bronze database 1788, and production silver database 1789, and a production gold database 1790. The set of databases may send data to the data ingest module 1758 and to the feature table refresh pipeline 1704.

In at least one embodiment, the model registry/model store 1791 may include sub-components such as a development model store database 1792 which may receive data from the tracking server module 1718, a staging model store database 1793, which may send data to the unit testing (CI) module 1728 and the CD pipeline 1744, and receive data from the integration test (CI) pipeline 1732. The sub-components of the model registry/model store 1791 may also include a production model store database 1794 which may receive data from the CD pipeline 1744. The model registry/model store 1791 may transmit data to the model server module 1795, which may, in turn, deliver data to the data ingest module 1758 and set of databases (e.g., elements 1786-1790) of the data platform 1781.

The source control pipeline 1796 may exchange data with the components of system 1700 and may include sub-components such as a development Git repository database 1797 which may send data to a staging Git repository database 1798. The staging Git repository database 1798 may data to a product Git repository database 1799 of the source control pipeline 1796.

Figure 18:
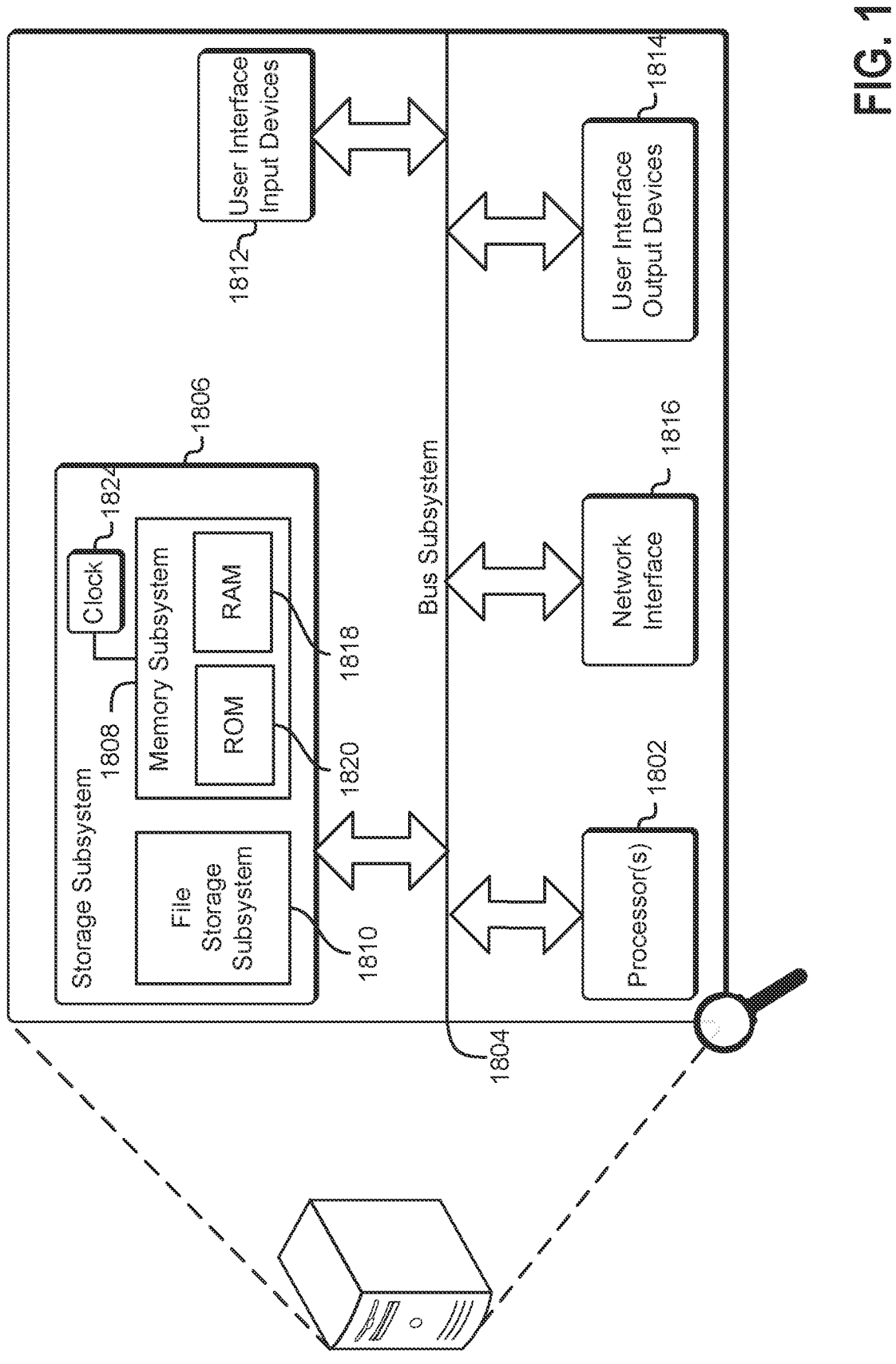
FIG. 18 illustrates a system in which various embodiments can be implemented.

FIG. 18 is an illustrative, simplified block diagram of a computing device 1800 that can be used to practice at least one embodiment of the present disclosure. In at least one embodiment the computing device 1800 may host any of the systems 100, 200, 300, 1600, and 1700 of FIGS. 1-3 and 16-17 described above. In various embodiments, the computing device 1800 includes any appropriate device operable to send and/or receive requests, messages, or information over an appropriate network and convey information back to a user of the device. The computing device 1800 may be used to implement any of the systems illustrated and described above. For example, the computing device 1800 may be configured for use as a data server, a web server, a portable computing device, a personal computer, a cellular or other mobile phone, a handheld messaging device, a laptop computer, a tablet computer, a set-top box, a personal data assistant, an embedded computer system, an electronic book reader, or any electronic computing device. The computing device 1800 may be implemented as a hardware device, a virtual computer system, or one or more programming modules executed on a computer system, and/or as another device configured with hardware and/or software to receive and respond to communications (e.g., web service application programming interface (API) requests) over a network.

As shown in FIG. 18, the computing device 1800 may include one or more processors 1802 that, in embodiments, communicate with and are operatively coupled to a number of peripheral subsystems via a bus subsystem. In some embodiments, these peripheral subsystems include a storage subsystem 1806, comprising a memory subsystem 1808 and a file/disk storage subsystem 1810, one or more user interface input devices 1812, one or more user interface output devices 1814, and a network interface subsystem 1816. Such storage subsystem 1806 may be used for temporary or long-term storage of information.

In some embodiments, the bus subsystem 1804 may provide a mechanism for enabling the various components and subsystems of computing device 1800 to communicate with each other as intended. Although the bus subsystem 1804 is shown schematically as a single bus, alternative embodiments of the bus subsystem utilize multiple buses. The network interface subsystem 1816 may provide an interface to other computing devices and networks. The network interface subsystem 1816 may serve as an interface for receiving data from and transmitting data to other systems from the computing device 1800. In some embodiments, the bus subsystem 1804 is utilized for communicating data such as details, search terms, and so on. In an embodiment, the network interface subsystem 1816 may communicate via any appropriate network that would be familiar to those skilled in the art for supporting communications using any of a variety of commercially available protocols, such as Transmission Control Protocol/Internet Protocol (TCP/IP), User Datagram Protocol (UDP), protocols operating in various layers of the Open System Interconnection (OSI) model, File Transfer Protocol (FTP), Universal Plug and Play (UPnP), Network File System (NFS), Common Internet File System (CIFS), and other protocols.

The network, in an embodiment, is a local area network, a wide-area network, a virtual private network, the Internet, an intranet, an extranet, a public switched telephone network, a cellular network, an infrared network, a wireless network, a satellite network, or any other such network and/or combination thereof, and components used for such a system may depend at least in part upon the type of network and/or system selected. In an embodiment, a connection-oriented protocol is used to communicate between network endpoints such that the connection-oriented protocol (sometimes called a connection-based protocol) is capable of transmitting data in an ordered stream. In an embodiment, a connection-oriented protocol can be reliable or unreliable. For example, the TCP protocol is a reliable connection-oriented protocol. Asynchronous Transfer Mode (ATM) and Frame Relay are unreliable connection-oriented protocols. Connection-oriented protocols are in contrast to packet-oriented protocols such as UDP that transmit packets without a guaranteed ordering. Many protocols and components for communicating via such a network are well known and will not be discussed in detail. In an embodiment, communication via the network interface subsystem 1816 is enabled by wired and/or wireless connections and combinations thereof.

In some embodiments, the user interface input devices 1812 include one or more user input devices such as a keyboard; pointing devices such as an integrated mouse, trackball, touchpad, or graphics tablet; a scanner; a barcode scanner; a touch screen incorporated into the display; audio input devices such as voice recognition systems, microphones; and other types of input devices. In general, use of the term "input device" is intended to include all possible types of devices and mechanisms for inputting information to the computing device 1800. In some embodiments, the one or more user interface output devices 1814 include a display subsystem, a printer, or non-visual displays such as audio output devices, etc. In some embodiments, the display subsystem includes a cathode ray tube (CRT), a flat-panel device such as a liquid crystal display (LCD), light emitting diode (LED) display, or a projection or other display device. In general, use of the term "output device" is intended to include all possible types of devices and mechanisms for outputting information from the computing device 1800. The one or more user interface output devices 1814 can be used, for example, to present user interfaces to facilitate user interaction with applications performing processes described and variations therein, when such interaction may be appropriate.

In some embodiments, the storage subsystem 1806 provides a computer-readable storage medium for storing the basic programming and data constructs that provide the functionality of at least one embodiment of the present disclosure. The applications (programs, code modules, instructions), when executed by one or more processors in some embodiments, provide the functionality of one or more embodiments of the present disclosure and, in embodiments, are stored in the storage subsystem 1806. These application modules or instructions can be executed by the one or more processors 1802. In various embodiments, the storage subsystem 1806 additionally provides a repository for storing data used in accordance with the present disclosure. In some embodiments, the storage subsystem 1806 comprises a memory subsystem 1808 and a file/disk storage subsystem 1810.

In embodiments, the memory subsystem 1808 includes a number of memories, such as a main random access memory (RAM) 1818 for storage of instructions and data during program execution and/or a read only memory (ROM) 1820, in which fixed instructions can be stored. In some embodiments, the file/disk storage subsystem 1810 provides a non-transitory persistent (non-volatile) storage for program and data files and can include a hard disk drive, a floppy disk drive along with associated removable media, a Compact Disk Read-Only Memory (CD-ROM) drive, an optical drive, removable media cartridges, or other like storage media.

In some embodiments, the computing device 1800 includes at least one local clock 1824. The at least one local clock 1824, in some embodiments, is a counter that represents the number of ticks that have transpired from a particular starting date and, in some embodiments, is located integrally within the computing device 1800. In various embodiments, the at least one local clock 1824 is used to synchronize data transfers in the processors for the computing device 1800 and the subsystems included therein at specific clock pulses and can be used to coordinate synchronous operations between the computing device 1800 and other systems in a data center. In another embodiment, the local clock is a programmable interval timer.

The computing device 1800 could be of any of a variety of types, including a portable computer device, tablet computer, a workstation, or any other device described below. Additionally, the computing device 1800 can include another device that, in some embodiments, can be connected to the computing device 1800 through one or more ports (e.g., USB, a headphone jack, Lightning connector, etc.). In embodiments, such a device includes a port that accepts a fiber-optic connector. Accordingly, in some embodiments, this device converts optical signals to electrical signals that are transmitted through the port connecting the device to the computing device 1800 for processing. Due to the ever-changing nature of computers and networks, the description of the computing device 1800 depicted in FIG. 18 is intended only as a specific example for purposes of illustrating the preferred embodiment of the device. Many other configurations having more or fewer components than the system depicted in FIG. 18 are possible.

The specification and drawings are, accordingly, to be regarded in an illustrative rather than a restrictive sense. However, it will be evident that various modifications and changes may be made thereunto without departing from the scope of the invention as set forth in the claims. Likewise, other variations are within the scope of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed but, on the contrary, the intention is to cover all modifications, alternative constructions and equivalents falling within the scope of the invention, as defined in the appended claims.

In some embodiments, data may be stored in a data store (not depicted). In some examples, a "data store" refers to any device or combination of devices capable of storing, accessing, and retrieving data, which may include any combination and number of data servers, databases, data storage devices, and data storage media, in any standard, distributed, virtual, or clustered system. A data store, in an embodiment, communicates with block-level and/or object-level interfaces. The computing device 1800 may include any appropriate hardware, software and firmware for integrating with a data store as needed to execute aspects of one or more applications for the computing device 1800 to handle some or all of the data access and business logic for the one or more applications. The data store, in an embodiment, includes several separate data tables, databases, data documents, dynamic data storage schemes, and/or other data storage mechanisms and media for storing data relating to a particular aspect of the present disclosure. In an embodiment, the computing device 1800 includes a variety of data stores and other memory and storage media as discussed above. These can reside in a variety of locations, such as on a storage medium local to (and/or resident in) one or more of the computers or remote from any or all of the computers across a network. In an embodiment, the information resides in a storage-area network (SAN) familiar to those skilled in the art, and, similarly, any necessary files for performing the functions attributed to the computers, servers or other network devices are stored locally and/or remotely, as appropriate.

In an embodiment, the computing device 1800 may provide access to content including, but not limited to, text, graphics, audio, video, and/or other content that is provided to a user in the form of HyperText Markup Language (HTML), Extensible Markup Language (XML), JavaScript, Cascading Style Sheets (CSS), JavaScript Object Notation (JSON), and/or another appropriate language. The computing device 1800 may provide the content in one or more forms including, but not limited to, forms that are perceptible to the user audibly, visually, and/or through other senses. The handling of requests and responses, as well as the delivery of content, in an embodiment, is handled by the computing device 1800 using PUP: Hypertext Preprocessor (PUP), Python, Ruby, Perl, Java, HTML, XML, JSON, JavaScript, and/or another appropriate language in this example. In an embodiment, operations described as being performed by a single device are performed collectively by multiple devices that form a distributed and/or virtual system.

In an embodiment, the computing device 1800 typically will include an operating system that provides executable program instructions for the general administration and operation of the computing device 1800 and includes a computer-readable storage medium (e.g., a hard disk, random access memory (RAM), read only memory (ROM), etc.) storing instructions that if executed (e.g., as a result of being executed) by a processor of the computing device 1800 cause or otherwise allow the computing device 1800 to perform its intended functions (e.g., the functions are performed as a result of one or more processors of the computing device 1800 executing instructions stored on a computer-readable storage medium).

In an embodiment, the computing device 1800 operates as a web server that runs one or more of a variety of server or mid-tier applications, including Hypertext Transfer Protocol (HTTP) servers, FTP servers, Common Gateway Interface (CGI) servers, data servers, Java servers, Apache servers, and business application servers. In an embodiment, computing device 1800 is also capable of executing programs or scripts in response to requests from user devices, such as by executing one or more web applications that are implemented as one or more scripts or programs written in any programming language, such as Java®, C, C# or C++, or any scripting language, such as Ruby, PUP, Perl, Python, JavaScript, or TCL, as well as combinations thereof.

In an embodiment, the computing device 1800 is capable of storing, retrieving, and accessing structured or unstructured data. In an embodiment, computing device 1800 additionally or alternatively implements a database, such as one of those commercially available from Oracle®, Microsoft®, Sybase®, and IBM® as well as open-source servers such as MySQL, Postgres, SQLite, MongoDB. In an embodiment, the database includes table-based servers, document-based servers, unstructured servers, relational servers, non-relational servers, or combinations of these and/or other database servers.

Embodiments of the disclosure can be described in view of the following clauses:

1. A computer-implemented method performed by a service provider to estimate target values for items, comprising:

obtaining, from a user of the service provider, a request to estimate a set of target values for a set of items that the user provides to clients of the user, the request including a user identifier usable by the service provider to:

identify the user from a plurality of users of the service provider;

identify, from a plurality of machine learning models of the service provider trained to output target value estimations, one or more machine learning models associated with the user; and identify a set of input types used by the one or more machine learning models to estimate the target values;

obtaining a set of input values corresponding the set of input types;

apportioning and combining the set of inputs according to predetermined groups to produce one or more grouped inputs;

inputting the one or more grouped inputs to the one or more machine learning models;

obtaining, as output from the plurality of machine learning models, a set of target values for the set of items; and providing the set of target values to the user.

2. The computer-implemented method of clause 1, wherein the set of input types includes one or more of:

a list of the set of items, geographical information relating to a geographical location of the user, client-specific information, or a set of initial values for the set of items.

3. The computer-implemented method of clause 1 or 2, wherein the one or more machine learning models are trained to output one or more of:

an estimated target value for an item, a recommendation for the item, a predicted side effect of the item, or a predicted interaction between the item and another item.

4. The computer-implemented method of any one of clauses 1-3, wherein:

obtaining the request includes receiving the request at one or more application programming interfaces (APIs); and the APIs assign the set of inputs and the user identifier to one or more components of a system implementing the computer-implemented method.

5. A system, comprising:

one or more processors; and memory that stores computer-executable instructions that, if executed by the one or more processors, cause the system to:

select a set of inputs from a plurality of inputs based on a user identifier of a user;

apportion and recombine the set of inputs to produce one or more grouped inputs;

input the one or more grouped inputs to one or more machine learning models selected based on the user identifier, the one or more machine learning models trained to generate predictions using the plurality of inputs; and provide individualized information that is output by the one or more machine learning models to the user.

6. The system of clause 5, wherein the executable instructions that apportion and recombine the set of inputs include instructions that apportion and recombine the set of inputs using criteria included in the plurality of inputs.

7. The system of clause 5 or 6, wherein the one or more machine learning models further:

receive outputs from one or more additional machine learning models; and use the outputs, in addition to the one or more grouped inputs, to determine the individualized information.

8. The system of clause 7, wherein the outputs from the one or more additional machine learning models include one or more of:

an item cluster, a characterization map, or an initial value of an item.

9. The system of any one of clauses 5-8, wherein the individualized information includes one or more of:

a target value for an item, a comparison of other values for the item, or a set of alternative items claim 5 to the item.

10. The system of any one of clauses 5-9, wherein the individualized information includes a target item value generated by the one or more machine learning models using an iterative process, the iterative process being used to re-compute a computed item value until a distance between the computed item value and optimization criteria no longer decreases.

11. The system of any one of clauses 5-10, wherein the individualized information includes a target item value generated using historical values that are included in the plurality of inputs.

12. The system of any one of clauses 5-11, wherein the individualized information includes a target item value generated using user similarity criteria included in the plurality of inputs.

13. The system of clause 12, wherein the system further implements an additional one or more machine learning models to:

estimate associated inputs from the plurality of inputs, the associated inputs being applicable to users assigned to a cluster of the user; and input the associated inputs to the one or more machine learning models.

14. A non-transitory computer-readable storage medium storing executable instructions that, as a result of being executed by one or more processors of a computer system, cause the computer system to at least:

obtain a request from a requestor to generate a target value for an item, the request including a user identifier and a plurality of inputs;

select one or more machine learning models and a set of inputs from the plurality of inputs using the user identifier, the one or more machine learning models having been trained to generate target values using the plurality of inputs;

apportion and recombine the set of inputs based on the user identifier, the one or more machine learning models, and predetermined categories to produce grouped inputs;

input the grouped inputs to the one or more machine learning models; and obtain the target value as an output from the one or more machine learning models to display the target value to the requestor.

15. The non-transitory computer-readable storage medium of clause 14, wherein:

the set of inputs comprise heterogeneous data obtained from different sources.

16. The non-transitory computer-readable storage medium of clause 14 or 15, wherein:

the set of inputs are assimilated and modified for apportioning and recombining based on one or more of:

format, syntax, or language.

17. The non-transitory computer-readable storage medium of any one of clauses 14-16, wherein the requestor is:

a user of a service provider that hosts the computer system, or a client of the user.

18. The non-transitory computer-readable storage medium of any one of clauses 14-17, wherein:

the executable instructions that cause the computer system to obtain the request include instructions that cause the computer system to receive the request via at least one application programming interface (API) call from a user interface; and the executable instructions further include instructions that further cause the computer system to provide, in response to the at least one API call, the target value to the user interface for display.

19. The non-transitory computer-readable storage medium of any one of clauses 14-18, wherein the target value is generated in real-time in response to obtaining the request.

20. The non-transitory computer-readable storage medium of any one of clauses 14-19, wherein the executable instructions further include instructions that further cause the computer system to:

select one or more additional machine learning models that:

use the plurality of inputs to group items of an item list into item clusters; and output the item clusters to the one or more machine learning models; and cause the one of the one or more machine learning models:

receive at least one of the item clusters; and generate an estimated value for the item cluster.

The various embodiments further can be implemented in a wide variety of operating environments, which in some cases can include one or more user computers, computing devices or processing devices that can be used to operate any of a number of applications. In an embodiment, user or client devices include any of a number of computers, such as desktop, laptop or tablet computers running a standard operating system, as well as cellular (mobile), wireless and handheld devices running mobile software and capable of supporting a number of networking and messaging protocols, and such a system also includes a number of workstations running any of a variety of commercially available operating systems and other known applications for purposes such as development and database management. In an embodiment, these devices also include other electronic devices, such as dummy terminals, thin-clients, gaming systems and other devices capable of communicating via a network, and virtual devices such as virtual machines, hypervisors, software containers utilizing operating-system level virtualization and other virtual devices or non-virtual devices supporting virtualization capable of communicating via a network.

In an embodiment, a system utilizes at least one network that would be familiar to those skilled in the art for supporting communications using any of a variety of commercially available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and other protocols. The network, in an embodiment, is a local area network, a wide-area network, a virtual private network, the Internet, an intranet, an extranet, a public switched telephone network, an infrared network, a wireless network, a satellite network, and any combination thereof. In an embodiment, a connection-oriented protocol is used to communicate between network endpoints such that the connection-oriented protocol (sometimes called a connection-based protocol) is capable of transmitting data in an ordered stream. In an embodiment, a connection-oriented protocol can be reliable or unreliable. For example, the TCP protocol is a reliable connection-oriented protocol. Asynchronous Transfer Mode ("ATM") and Frame Relay are unreliable connection-oriented protocols. Connection-oriented protocols are in contrast to packet-oriented protocols such as UDP that transmit packets without a guaranteed ordering.

In an embodiment, the system utilizes a web server that runs one or more of a variety of server or mid-tier applications, including Hypertext Transfer Protocol ("HTTP") servers, FTP servers, Common Gateway Interface ("CGI") servers, data servers, Java servers, Apache servers, and business application servers. In an embodiment, the one or more servers are also capable of executing programs or scripts in response to requests from user devices, such as by executing one or more web applications that are implemented as one or more scripts or programs written in any programming language, such as Java®, C, C# or C++, or any scripting language, such as Ruby, PUP, Perl, Python or TCL, as well as combinations thereof. In an embodiment, the one or more servers also include database servers, including without limitation those commercially available from Oracle®, Microsoft®, Sybase®, and IBM® as well as open-source servers such as MySQL, Postgres, SQLite, MongoDB, and any other server capable of storing, retrieving, and accessing structured or unstructured data. In an embodiment, a database server includes table-based servers, document-based servers, unstructured servers, relational servers, non-relational servers, or combinations of these and/or other database servers.

In an embodiment, the system includes a variety of data stores and other memory and storage media as discussed above that can reside in a variety of locations, such as on a storage medium local to (and/or resident in) one or more of the computers or remote from any or all of the computers across the network. In an embodiment, the information resides in a storage-area network ("SAN") familiar to those skilled in the art and, similarly, any necessary files for performing the functions attributed to the computers, servers or other network devices are stored locally and/or remotely, as appropriate. In an embodiment where a system includes computerized devices, each such device can include hardware elements that are electrically coupled via a bus, the elements including, for example, at least one central processing unit ("CPU" or "processor"), at least one input device (e.g., a mouse, keyboard, controller, touch screen, or keypad), at least one output device (e.g., a display device, printer, or speaker), at least one storage device such as disk drives, optical storage devices, and solid-state storage devices such as random access memory ("RAM") or read-only memory ("ROM"), as well as removable media devices, memory cards, flash cards, etc., and various combinations thereof.

In an embodiment, such a device also includes a computer-readable storage media reader, a communications device (e.g., a modem, a network card (wireless or wired), an infrared communication device, etc.), and working memory as described above where the computer-readable storage media reader is connected with, or configured to receive, a computer-readable storage medium, representing remote, local, fixed, and/or removable storage devices as well as storage media for temporarily and/or more permanently containing, storing, transmitting, and retrieving computer-readable information. In an embodiment, the system and various devices also typically include a number of software applications, modules, services, or other elements located within at least one working memory device, including an operating system and application programs, such as a client application or web browser. In an embodiment, customized hardware is used and/or particular elements are implemented in hardware, software (including portable software, such as applets), or both. In an embodiment, connections to other computing devices such as network input/output devices are employed.

In an embodiment, storage media and computer readable media for containing code, or portions of code, include any appropriate media known or used in the art, including storage media and communication media, such as but not limited to volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the resent disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed but, on the contrary, the intention is to cover all modifications, alternative constructions, and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. Similarly, use of the term "or" is to be construed to mean "and/or" unless contradicted explicitly or by context. The terms "comprising," "having," "including," and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal. The use of the phrase "based on," unless otherwise explicitly stated or clear from context, means "based at least in part on" and is not limited to "based solely on."

Conjunctive language, such as phrases of the form "at least one of A, B, and C," or "at least one of A, B and C," (i.e., the same phrase with or without the Oxford comma) unless specifically stated otherwise or otherwise clearly contradicted by context, is otherwise understood within the context as used in general to present that an item, term, etc., may be either A or B or C, any nonempty subset of the set of A and B and C, or any set not contradicted by context or otherwise excluded that contains at least one A, at least one B, or at least one C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}, and, if not contradicted explicitly or by context, any set having {A}, {B}, and/or {C} as a subset (e.g., sets with multiple "A"). Thus, such conjunctive language is not generally intended to imply that certain embodiments require at least one of A, at least one of B and at least one of C each to be present. Similarly, phrases such as "at least one of A, B, or C" and "at least one of A, B or C" refer to the same as "at least one of A, B, and C" and "at least one of A, B and C" refer to any of the following sets: {A}, {B}, {C}, {A, B}, {A, C}, {B, C}, {A, B, C}, unless differing meaning is explicitly stated or clear from context. In addition, unless otherwise noted or contradicted by context, the term "plurality" indicates a state of being plural (e.g., "a plurality of items" indicates multiple items). The number of items in a plurality is at least two but can be more when so indicated either explicitly or by context.

Operations of processes described herein can be performed in any suitable order unless otherwise indicated herein or otherwise clearly contradicted by context. In an embodiment, a process such as those processes described herein (or variations and/or combinations thereof) is performed under the control of one or more computer systems configured with executable instructions and is implemented as code (e.g., executable instructions, one or more computer programs or one or more applications) executing collectively on one or more processors, by hardware or combinations thereof. In an embodiment, the code is stored on a computer-readable storage medium, for example, in the form of a computer program comprising a plurality of instructions executable by one or more processors. In an embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In an embodiment, code (e.g., executable code or source code) is stored on a set of one or more non-transitory computer-readable storage media having stored thereon executable instructions that, when executed (i.e., as a result of being executed) by one or more processors of a computer system, cause the computer system to perform operations described herein. The set of non-transitory computer-readable storage media, in an embodiment, comprises multiple non-transitory computer-readable storage media, and one or more of individual non-transitory storage media of the multiple non-transitory computer-readable storage media lack all of the code while the multiple non-transitory computer-readable storage media collectively store all of the code. In an embodiment, the executable instructions are executed such that different instructions are executed by different processors for example, a non-transitory computer-readable storage medium stores instructions and a main CPU executes some of the instructions while a graphics processor unit executes other instructions. In another embodiment, different components of a computer system have separate processors and different processors execute different subsets of the instructions.

Accordingly, in an embodiment, computer systems are configured to implement one or more services that singly or collectively perform operations of processes described herein, and such computer systems are configured with applicable hardware and/or software that enable the performance of the operations. Further, a computer system, in an embodiment of the present disclosure, is a single device and, in another embodiment, is a distributed computer system comprising multiple devices that operate differently such that the distributed computer system performs the operations described herein and such that a single device does not perform all operations.

The use of any and all examples or exemplary language (e.g., "such as") provided herein is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references including publications, patent applications, and patents cited herein are hereby incorporated by reference to the same extent as if each reference were individually and specifically indicated to be incorporated by reference and were set forth in its entirety herein.

What is claimed is:

1. A computer-implemented method performed by a service provider to estimate target values for items, comprising:

obtaining, from a user of the service provider, a request to estimate a set of target values for a set of items that the user provides to clients of the user, the request including a user identifier usable by the service provider to:
identify the user from a plurality of users of the service provider;
identify, from a plurality of machine learning models of the service provider trained to output target value estimations, one or more machine learning models associated with the user; and
identify a set of input types used by the one or more machine learning models to estimate the target values;
obtaining a set of input values corresponding the set of input types;
apportioning and combining the set of inputs according to predetermined groups to produce one or more grouped inputs;
monitoring performance of the one or more machine learning models associated with the user based on feedback signals and measurements from prior estimations to detect model performance drift;
updating the one or more machine learning models associated with the user by retraining with updated inputs and deploying an updated model instance responsive to the detected model performance drift;
inputting the one or more grouped inputs to the updated model instance;
obtaining, as output from the updated model instance, a set of target values for the set of items; and
providing the set of target values to the user.

2. The computer-implemented method of claim 1, wherein the set of input types includes one or more of:
a list of the set of items,
geographical information relating to a geographical location of the user, client-specific information, or
a set of initial values for the set of items.

3. The computer-implemented method of claim 1, wherein the updated model instance is trained to output one or more of:
an estimated target value for an item,
a recommendation for the item,
a predicted side effect of the item, or
a predicted interaction between the item and another item.

4. The computer-implemented method of claim 1, wherein:
obtaining the request includes receiving the request at one or more application programming interfaces (APIs); and
the APIs assign the set of inputs and the user identifier to one or more components of a system implementing the computer-implemented method.

5. A system, comprising:
one or more processors; and
memory that stores computer-executable instructions that, if executed by the one or more processors, cause the system to:
select a set of inputs from a plurality of inputs based on a user identifier of a user;
apportion and recombine the set of inputs to produce one or more grouped inputs;
monitor performance of one or more machine learning models associated with the user based on feedback signals and measurements from prior predictions to detect model performance drift;
update the one or more machine learning models associated with the user by retraining with updated inputs and deploying an updated model instance responsive to the detected model performance drift;

input the one or more grouped inputs to the updated model instance, the updated model instance trained to generate predictions using the plurality of inputs; and
provide individualized information that is output by the updated model instance to the user.

6. The system of claim 5, wherein the executable instructions that apportion and recombine the set of inputs include instructions that apportion and recombine the set of inputs using criteria included in the plurality of inputs.

7. The system of claim 5, wherein the updated model instance further:
receive outputs from one or more additional machine learning models; and
use the outputs, in addition to the one or more grouped inputs, to determine the individualized information.

8. The system of claim 7, wherein the outputs from the one or more additional machine learning models include one or more of:
an item cluster,
a characterization map, or
an initial value of an item.

9. The system of claim 5, wherein the individualized information includes one or more of:
a target value for an item,
a comparison of other values for the item, or
a set of alternative items to the item.

10. The system of claim 5, wherein the individualized information includes a target item value generated by the updated model instance using an iterative process, the iterative process being used to re-compute a computed item value until a distance between the computed item value and optimization criteria no longer decreases.

11. The system of claim 5, wherein the individualized information includes a target item value generated using historical values that are included in the plurality of inputs.

12. The system of claim 5, wherein the individualized information includes a target item value generated using user similarity criteria included in the plurality of inputs.

13. The system of claim 12, wherein the system further implements an additional one or more machine learning models to:
estimate associated inputs from the plurality of inputs, the associated inputs being applicable to users assigned to a cluster of the user; and
input the associated inputs to the updated model instance.

14. A non-transitory computer-readable storage medium storing executable instructions that, as a result of being executed by one or more processors of a computer system, cause the computer system to at least:
obtain a request from a requestor to generate a target value for an item, the request including a user identifier and a plurality of inputs;
select one or more machine learning models and a set of inputs from the plurality of inputs using the user identifier, the one or more machine learning models having been trained to generate target values using the plurality of inputs;
apportion and recombine the set of inputs based on the user identifier, the one or more machine learning models, and predetermined categories to produce grouped inputs;
monitor performance of the one or more machine learning models based on feedback signals and measurements from prior target values to detect model performance drift;

update the one or more machine learning models by retraining with updated inputs and deploying an updated model instance responsive to the detected model performance drift;

input the grouped inputs to the updated model instance; and obtain the target value as an output from the updated model instance to display the target value to the requestor.

15. The non-transitory computer-readable storage medium of claim 14, wherein:

the set of inputs comprise heterogeneous data obtained from different sources.

16. The non-transitory computer-readable storage medium of claim 14, wherein:

the set of inputs are assimilated and modified for apportioning and recombining based on one or more of:

format, syntax, or p1 language.

17. The non-transitory computer-readable storage medium of claim 14, wherein the requestor is:

a user of a service provider that hosts the computer system, or a client of the user.

18. The non-transitory computer-readable storage medium of claim 14, wherein:

44 the executable instructions that cause the computer system to obtain the request include instructions that cause the computer system to receive the request via at least one application programming interface (API) call from a user interface; and the executable instructions further include instructions that further cause the computer system to provide, in response to the at least one API call, the target value to the user interface for display.

19. The non-transitory computer-readable storage medium of claim 14, wherein the target value is generated in real-time in response to obtaining the request.

20. The non-transitory computer-readable storage medium of claim 14, wherein the executable instructions further include instructions that further cause the computer system to:

select one or more additional machine learning models that:

use the plurality of inputs to group items of an item list into item clusters; and output the item clusters to the updated model instance; and cause the updated model instance:

receive at least one of the item clusters; and generate an estimated value for the item cluster.

* * * * *